(12) United States Patent
Ozeki et al.

(10) Patent No.: US 9,295,734 B2
(45) Date of Patent: Mar. 29, 2016

(54) BRANCHED AMPHIPATHIC BLOCK POLYMER AND MOLECULAR AGGREGATE AND DRUG DELIVERY SYSTEM USING SAME

(75) Inventors: Eiichi Ozeki, Kyoto (JP); Shunsaku Kimura, Hirakata (JP); Akira Makino, Kyoto (JP)

(73) Assignees: SHIMADZU CORPORATION, Kyoto (JP); KYOTO UNIVERSITY, Kyoto (JP)

( * ) Notice: Subject to any disclaimer, the term of this patent is extended or adjusted under 35 U.S.C. 154(b) by 46 days.

(21) Appl. No.: 14/126,803

(22) PCT Filed: Jun. 22, 2012

(86) PCT No.: PCT/JP2012/066023
§ 371 (c)(1),
(2), (4) Date: Dec. 16, 2013

(87) PCT Pub. No.: WO2012/176885
PCT Pub. Date: Dec. 27, 2012

(65) Prior Publication Data
US 2014/0127132 A1      May 8, 2014

(30) Foreign Application Priority Data
Jun. 23, 2011   (JP) ................................. 2011-139468

(51) Int. Cl.
| | |
|---|---|
| A61K 8/00 | (2006.01) |
| A61K 49/00 | (2006.01) |
| A61K 9/107 | (2006.01) |
| B82Y 40/00 | (2011.01) |
| A61K 47/34 | (2006.01) |
| A61K 9/51 | (2006.01) |
| C08L 101/00 | (2006.01) |
| A61K 49/12 | (2006.01) |
| A61K 47/48 | (2006.01) |
| C08G 83/00 | (2006.01) |

(52) U.S. Cl.
CPC ........... *A61K 49/0002* (2013.01); *A61K 9/1075* (2013.01); *A61K 9/5153* (2013.01); *A61K 47/34* (2013.01); *A61K 49/0082* (2013.01); *B82Y 40/00* (2013.01); *C08G 83/008* (2013.01); *C08L 101/005* (2013.01); *A61K 47/48253* (2013.01); *A61K 49/124* (2013.01); *C08G 83/005* (2013.01); *Y10S 424/16* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 2004/0247624 A1* | 12/2004 | Unger et al. | 424/400 |
| 2005/0137133 A1 | 6/2005 | MacDonald et al. | |
| 2006/0040866 A1 | 2/2006 | MacDonald et al. | |
| 2008/0019908 A1 | 1/2008 | Akitsu et al. | |
| 2011/0104056 A1 | 5/2011 | Hara et al. | |

FOREIGN PATENT DOCUMENTS

| | | |
|---|---|---|
| JP | 2007-504132 A | 3/2007 |
| JP | 2008-24816 A | 2/2008 |
| JP | 2009-504650 A | 2/2009 |
| WO | WO-2005/023834 A2 | 3/2005 |
| WO | WO-2009/148121 A1 | 12/2009 |

OTHER PUBLICATIONS

International Search Report for Application No. PCT/JP2012/066023 mailed Jul. 31, 2012.
Makino, Akira et al., "Near-infrared fluorescence tumor imaging using nanocarrier composed of poly(L-lactic acid)-block-poly(sarcosine) amphiphilic polydesipeptide", Biomaterials, 2009, vol. 30, pp. 5156-5160.
Koide, Hiroyuki et al., "Elucidation of Accelerated Blood Clearance Phenomenon Caused by Repeat Injection of PEGylated Nanocarriers", Yakugaku Zasshi, 2009, vol. 129, No. 12, pp. 1445-1451.
Makino, Akira et al., "Preparation of Novel Polymer Assemblies, "Lactosome", Composed of Poly(L-lactic acid) and Poly(sarcosine)", Chemistry Letters, 2007, vol. 36, No. 10, pp. 1220-1221.
English Translation of Written Opinion of the International Searching Authority (PCT/ISA/237) for Application No. PCT/JP2012/066023 mailed Jan. 9, 2014.
Supplementary European Search Report for the Application No. EP 12 80 2877 dated Sep. 26, 2014.

* cited by examiner

*Primary Examiner* — James Rogers
(74) *Attorney, Agent, or Firm* — Cheng Law Group, PLLC

(57) ABSTRACT

Provided is a polymeric micelle pharmaceutical preparation that can increase the ratio of contrast at tumor site to background contrast in a short period of time after administration of a lactosome and can suppress the ABC phenomenon so that the lactosome can be administered more than once within a short span. A branched-type amphiphilic block polymer comprising: a multi-branched hydrophilic block comprising sarcosine; and a hydrophobic block comprising polylactic acid. The branched-type amphiphilic block polymer, wherein the number of branches of the hydrophilic block is 3. A molecular assembly comprising the branched-type amphiphilic block polymer. The molecular assembly further comprising a linear type amphiphilic block polymer.

10 Claims, 13 Drawing Sheets

Plasma: Collected one week after administration (1/27)
Plate: A3B 0.5 μg/well

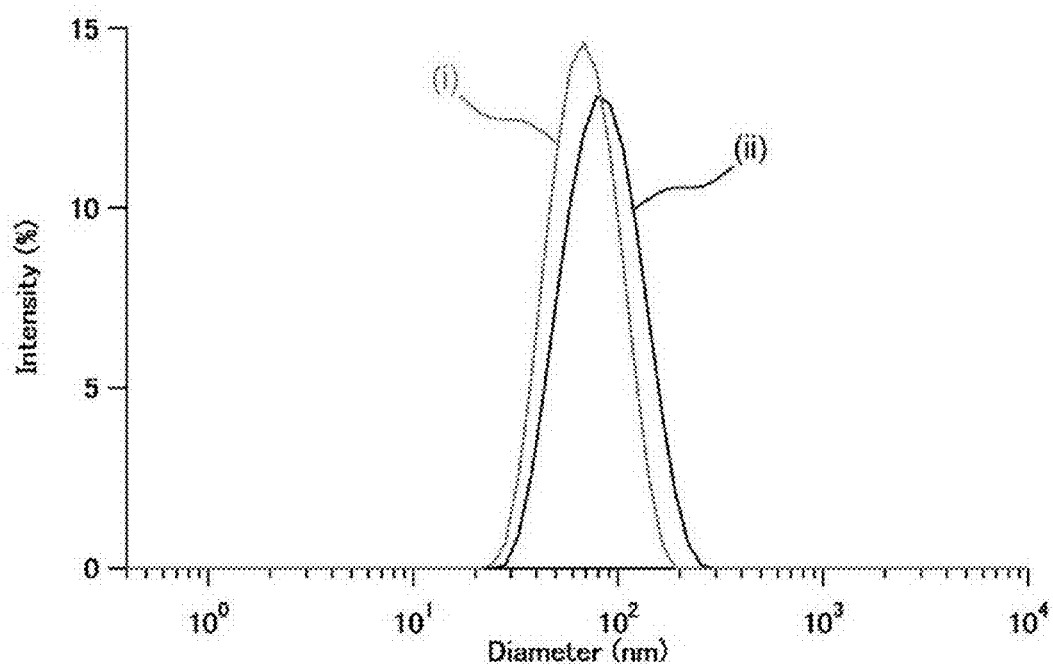

BRANCHED AMPHIPATHIC BLOCK POLYMER AND MOLECULAR AGGREGATE AND DRUG DELIVERY SYSTEM USING SAME

TECHNICAL FIELD

The present invention belongs to the fields of supramolecular chemistry, collaborative region of medicine, engineering and pharmacy, and nanomedicine. The present invention relates to a nano-carrier as a molecular probe for molecular imaging, a nano-carrier for drug delivery, and a dispersing agent for hydrophobic compounds. More specifically, the present invention relates to a branched-type amphiphilic block polymer, a molecular assembly using the same, and a drug delivery system.

BACKGROUND ART

WO 2009/148121 (Patent Document 1) and Biomaterials, 2009, Vol. 30, p. 5156-5160 (Non-Patent Document 1) disclose that an amphiphilic block polymer having a polylactic acid chain as a hydrophobic block and a polysarcosine chain as a hydrophilic block self-assembles in an aqueous solution to form a polymeric micelle (lactosome) having a particle size of 30 nm or more. It is known that the lactosomes exhibit high retentivity in blood and the amount of the lactosomes accumulated in the liver is significantly reduced as compared to polymeric micelles that have been already developed. The lactosomes utilize the property that nanoparticles with a particle size of several tens of nanometers to several hundreds of nanometers retained in blood are likely to be accumulated in cancer (Enhanced Permeation and Retention (EPR) effect), and therefore can be used as nano-carriers for cancer site-targeting molecular imaging or drug delivery.

A phenomenon, namely "Accelerated Blood Clearance (ABC) phenomenon" is known, in which an immune system is activated by administering polymeric micelles composed of a synthetic polymer to a living body once so that when the same polymeric micelles are administered again, they are accumulated in the liver due to the action of the immune system. Details of the mechanism of development of this ABC phenomenon are more or less clarified. YAKUGAKU ZASSHI, 2009, Vol. 129, No. 12, p. 1445-1451 (Non-Patent Document 2) reports that the development of the ABC phenomenon is suppressed when polymeric micelles having a particle size of 30 nm or less are used.

PRIOR ART DOCUMENTS

Patent Document

Patent Document 1: WO 2009/148121

Non-Patent Documents

Non-Patent Document 1: Biomaterials, 2009, Vol. 30, p. 5156-5160
Non-Patent Document 2: YAKUGAKU ZASSHI, 2009, Vol. 129, No. 12, p. 1445-1451

SUMMARY OF THE INVENTION

Problems to be Solved by the Invention

The lactosomes described in Patent Document 1 and Non-Patent Document 1 exhibit very high retentivity in blood, and therefore it takes time to reduce background signals. Specifically, the ratio of contrast at cancer site to background contrast is maximized 24 hours after administration of the lactosomes.

Therefore, it is difficult to perform imaging in a short period of time.

Particularly, it is difficult to use the lactosomes as nano-carriers as molecular probes for imaging (radiodiagnosis) using a short-half-life radionuclide, such as 18F-PET (18F has a half-life of 110 minutes).

Further, also in the case of the lactosomes (as in the case of polymeric micelles composed of a synthetic polymer), the ABC phenomenon occurs.

Therefore, there is a problem that the lactosomes cannot be administered more than once while an immunological memory effect is reduced.

It is therefore an object of the present invention to create a polymeric micelle pharmaceutical preparation that can increase the ratio of contrast at tumor site to background contrast in a short period of time after administration of a lactosome and can suppress the ABC phenomenon so that the lactosome can be administered more than once within a short span.

Means for Solving the Problems

The present inventors have intensively studied, and as a result, have found that the above object of the present invention can be achieved by molecularly designing an amphiphilic block polymer so that its hydrophilic block has a branched structure constituted from a plurality of sarcosine chains, which has led to the completion of the present invention.

The present invention includes the followings.

(1) A branched-type amphiphilic block polymer comprising:
   a branched hydrophilic block comprising sarcosine; and
   a hydrophobic block comprising polylactic acid.

(2) The branched-type amphiphilic block polymer according to (1), wherein the hydrophilic block comprising 2 to 200 sarcosine units in total.

(3) The branched-type amphiphilic block polymer according to (1) or (2), wherein the number of branches of the hydrophilic block is 3.

(4) The branched-type amphiphilic block polymer according to any one of (1) to (3), wherein lactic acid units constituting the polylactic acid are 10 to 400.

(5) The branched-type amphiphilic block polymer according to any one of (1) to (4), wherein the hydrophobic block is not branched.

(6) The branched-type amphiphilic block polymer according to (5), wherein the plurality of hydrophilic blocks extend as branches from one carbon atom in a molecular chain containing the polylactic acid chain of the hydrophobic block.

(7) The branched-type amphiphilic block polymer according to (6), which has a structure represented by the following formula (I):

[Chemical formula 1]

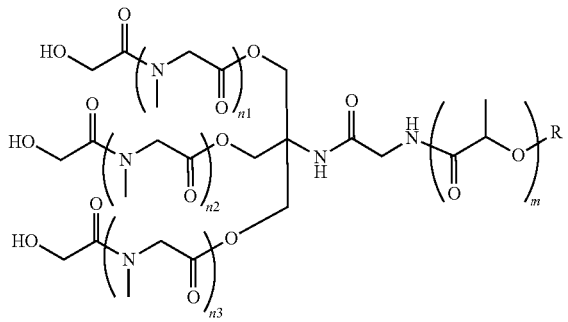

(I)

wherein n1, n2 and n3 represent numbers whose sum is 3 to 200, m represents a number of 15 to 60, and R represents a hydrogen atom or an organic group.

(8) The branched-type amphiphilic block polymer according to any one of (1) to (7), wherein a ratio of a total number of the sarcosine units contained in the hydrophilic block to a total number of the lactic acid units contained in the hydrophobic block is 0.05 or more and less than 1.8.

(9) A molecular assembly comprising the branched-type amphiphilic block polymer according to (1) to (8).

(10) The molecular assembly according to (9), further comprising a linear type amphiphilic block polymer comprising one polysarcosine chain as a hydrophilic block and one polylactic acid chain as a hydrophobic block.

(11) The molecular assembly according to (9) or (10), which encapsulates a functional substance selected from the group consisting of a signal agent and a drug.

(12) The molecular assembly according to (11), wherein the substance has a polylactic acid chain.

(13) The molecular assembly according to (9) or (10), wherein the branched-type amphiphilic block polymer has a functional group selected from the group consisting of a signal group and a ligand group.

(14) The molecular assembly according to any one of (9) to (13), whose particle size is 10 to 50 nm.

(15) The molecular assembly according to any one of (9) to (14), which is obtained by a preparation method comprising the steps of:

preparing a solution, in a container, containing the branched-type amphiphilic block polymer in an organic solvent;

removing the organic solvent from the solution to obtain a film comprising the branched-type amphiphilic block polymer on an inner wall of the container; and adding water or an aqueous solution into the container and performing ultrasonic treatment to convert the film into a molecular assembly, thereby obtaining a dispersion liquid of the molecular assembly.

(16) The molecular assembly according to anyone of (9) to (14), which is obtained by a preparation method comprising the steps of:

preparing a solution, in a container, containing the branched-type amphiphilic block polymer in an organic solvent;

dispersing the solution into water or an aqueous solution; and removing the organic solvent.

(17) A drug delivery system comprising administering the molecular assembly according to any one of (11) to (16) as a molecular probe to a non-human animal.

Effects of the Invention

According to the present invention, the branched structure of the hydrophilic block makes it possible to prepare a lactosome having a small particle size (e.g., a particle size less than 30 nm) that conventional lactosomes cannot have. Therefore, the number of the lactosomes that leak through gaps in blood vessel walls around cancer cells is increased, which makes it possible to increase the rate of accumulation of the lactosomes in a cancer site. Further, the distribution of the lactosomes in thinner blood vessels is accelerated and therefore the lactosomes are distributed throughout the body, which makes it possible to reduce background signals. That is, it is possible to increase the ratio of contrast at tumor site to background contrast. This makes it possible to achieve short-time imaging.

Further, according to the present invention, the branched structure of the hydrophilic block makes it possible to prepare a lactosome having, in its surface, a dense polymer brush structure of sarcosine chains. Therefore, the development of the ABC phenomenon can be suppressed irrespective of whether or not the particle size is less than 30 nm.

Therefore, according to the present invention, it is possible to create a polymeric micelle preparation that can increase the ratio of contrast at tumor site to background contrast in a short period of time after administration of lactosomes and can suppress the ABC phenomenon so that the lactosomes can be administered more than once within a short span.

BRIEF DESCRIPTION OF THE DRAWINGS

FIG. 13 shows the results of DLS measurement of branched single-type molecular assembly prepared in Example 9 and composed of only a branched-type amphiphilic block polymer.

MODE FOR CARRYING OUT THE INVENTION

[1. Branched-Type Amphiphilic Block Polymer]

Figure 1:
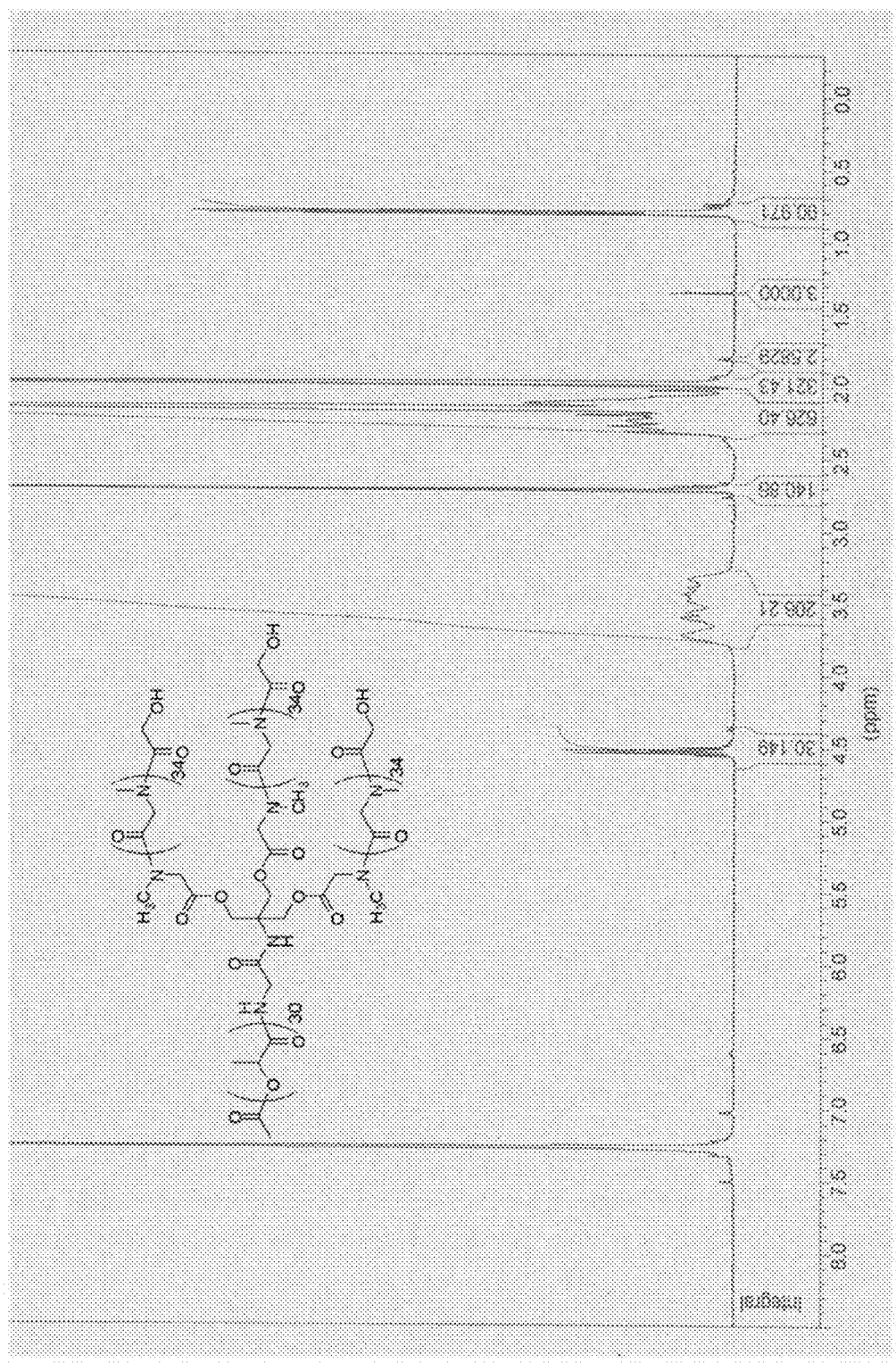
FIG. 1 is a $^1$H NMR spectrum of a branched-type amphiphilic block polymer synthesized in Example 1.

An amphiphilic block polymer according to the present invention comprises a branched hydrophilic block comprising sarcosine, and a hydrophobic block comprising polylactic acid. The hydrophilic block and the hydrophobic block are linked together by a linker part.

[1-1. Hydrophilic Block]

In the present invention, the specific degree of the physical property, "hydrophilicity" of the hydrophilic block of the branched-type amphiphilic block polymer is not particularly limited, but, at least, the whole hydrophilic block shall be relatively more hydrophilic than a polylactic acid chain as the hydrophobic block that will be described later. Alternatively, the hydrophilic block shall be hydrophilic to such an extent that a copolymer composed of the hydrophilic block and the hydrophobic block can have amphiphilicity as a whole molecule of the copolymer. Alternatively, the hydrophilic block shall be hydrophilic to such an extent that the amphiphilic block polymer can self-assemble in a solvent to form a self-assembly, particularly, a particulate self-assembly.

The amphiphilic block polymer according to the present invention has a branched structure in the hydrophilic block. Each of the branches of the hydrophilic block contains sarcosine.

The kinds and ratio of structural units constituting the hydrophilic block are appropriately determined by those skilled in the art so that a resultant block can have such hydrophilicity as described above as a whole. Specifically, the total number of sarcosine units contained in all the branches may be, for example, 2 to 200, 2 to 100, or 2 to 10. Alternatively, the total number of sarcosine units contained in the plurality of hydrophilic blocks may be, for example, 30 to 200 or 50 to 100. The average number of sarcosine units per one branch may be, for example, 1 to 60, 1 to 30, 1 to 10, or 1 to 6. That is, each of the hydrophilic blocks can be formed to contain sarcosine or a polysarcosine chain.

If the number of structural units exceeds the above range, when a molecular assembly is formed, the resultant molecular assembly tends to lack stability. If the number of structural units is less than the above range, a resultant block polymer cannot serve as an amphiphilic block polymer or formation of a molecular assembly tends to be difficult per se.

The number of branches of the hydrophilic block shall be 2 or more, but is preferably 3 or more from the viewpoint of efficiently obtaining a particulate micelle when a molecular assembly is formed. The upper limit of the number of branches of the hydrophilic block is not particularly limited, but is, for example, 27. Particularly, in the present invention, the number of branches of the hydrophilic block is preferably 3.

Sarcosine (i.e., N-methylglycine) is highly water-soluble, and polymer of sarcosine is highly flexible, because said polymer has an N-substituted amide and therefore can be more easily cis-trans isomerized as compared to a normal amide group, and steric hindrance around the $C^\alpha$ carbon atom is low. The use of such a structure as a constituent block is very useful in that the block can have high hydrophilicity as its basic characteristic, or both high hydrophilicity and high flexibility as its basic characteristics.

Further, the hydrophilic block preferably has hydrophilic groups (typified by, for example, hydroxyl groups) at its end (i.e., at the end opposite to the linker part).

In the polysarcosine chain, all the sarcosine units may be either continuous or discontinuous. However, it is preferred that the polypeptide chain is molecularly-designed so that the basic characteristics thereof described above are not impaired as a whole.

[1-2. Hydrophobic Block]

In the present invention, the specific degree of the physical property, "hydrophobicity" of the hydrophobic block is not particularly limited, but, at least, the hydrophobic block shall be hydrophobic enough to be a region relatively more hydrophobic than the whole hydrophilic block so that a copolymer composed of the hydrophilic block and the hydrophobic block can have amphiphilicity as a whole molecule of the copolymer, or so that the amphiphilic block polymer can self-assemble in a solvent to form a self-assembly, preferably a particulate self-assembly.

The hydrophobic block present in one amphiphilic block polymer may or may not be branched.

In the present invention, the hydrophobic block contains a polylactic acid chain. The kinds and ratio of structural units constituting the hydrophobic block are appropriately determined by those skilled in the art so that a resultant block can have such hydrophobicity as described above as a whole. Specifically, for example, when the hydrophobic block is not branched, the number of lactic acid units may be, for example, 5 to 100, 15 to 60, or 25 to 45. When the hydrophobic block is branched, the total number of lactic acid units contained in all the branches may be, for example, 10 to 400, and preferably 20 to 200. In this case, the average number of lactic acid units per one branch is, for example, 5 to 100, and preferably 10 to 100.

If the number of structural units exceeds the above range, when a molecular assembly is formed, the resultant molecular assembly tends to lack stability. If the number of structural units is less than the above range, formation of a molecular assembly tends to be difficult per se.

When the hydrophobic block is branched, the number of branches is not particularly limited, but may be, for example, equal to or less than the number of branches of the hydrophilic block from the viewpoint of efficiently obtaining a particulate micelle when a molecular assembly is formed.

Polylactic acid has the following basic characteristics.

Polylactic acid has excellent biocompatibility and stability. Therefore, a molecular assembly obtained from the amphiphilic material containing polylactic acid as a constituent block is very useful from the viewpoint of applicability to a living body, especially a human body.

Further, polylactic acid is rapidly metabolized due to its excellent biodegradability, and is therefore less likely to accumulate in tissue other than cancer tissue in a living body. Therefore, a molecular assembly obtained from the amphiphilic material containing polylactic acid as a constituent block is very useful from the viewpoint of specific accumulation in cancer tissue.

Further, polylactic acid is excellent in solubility in low-boiling point solvents. This makes it possible to avoid the use of a hazardous high-boiling point solvent when a molecular assembly is produced from the amphiphilic material containing polylactic acid as a constituent block. Therefore, such a molecular assembly is very useful from the viewpoint of safety for a living body.

In the polylactic acid chain, all the lactic acid units may be either continuous or discontinuous. However, it is preferred that the polypeptide chain is molecularly-designed so that the basic characteristics thereof described above are not impaired as a whole.

From the viewpoint of optical purity, the hydrophobic block chain may include the following variations.

For example, the lactic acid units constituting the hydrophobic block chain may include only L-lactic acid units, or may include only D-lactic acid units, or may include both L-lactic acid units and D-lactic acid units. The hydrophobic block may be used singly or in combination of two or more of them selected from the above examples.

In a case where the lactic acid units include both L-lactic acid units and D-lactic acid units, the order of polymerization of L-lactic acid units and D-lactic acid units is not particularly limited. For example, L-lactic acid units and D-lactic acid units may be polymerized so that one or two L-lactic acid units and one or two D-lactic acid units are alternately arranged, or may be randomly polymerized, or may be block-polymerized.

Therefore, in a case where the lactic acid units include both L-lactic acid units and D-lactic acid units, the amount of each of the lactic acid units is not particularly limited. That is, the amount of L-lactic acid units contained in the hydrophobic block chain and the amount of D-lactic acid units contained in the hydrophobic block chain may be different from each other, or may be the same, and in this case the 10 or more lactic acid units may be a racemate having an optical purity of 0% as a whole.

[1-3. Ratio of Number of Sarcosine Units to Number of Lactic Acid Units]

In the amphiphilic block polymer according to the present invention, when the number of sarcosine units (i.e., the total number of sarcosine units contained in all the branches of the hydrophilic block) is defined as $N^S$ and the number of lactic acid units (i.e., the number of lactic acid units contained in the hydrophobic block, or the total number of lactic acid units contained in all the branches when the hydrophobic block is branched) is defined as $N^L$, the ratio of $N^S/N^L$ may be, for example, 0.05 to 5 or 0.05 to 4.

More preferably, the ratio of $N^S/N^L$ may be 0.05 or more and less than 1.8, for example, 0.05 or more and 1.7 or less, 0.05 or more and 1.67 or less, 0.1 or more and 1.7 or less, or 0.1 or more and 1.67 or less.

[1-4. Branched Structure]

The structure of the linker site that links the hydrophilic block and the hydrophobic block together is not particularly limited as long as it is a chemically acceptable structure.

For example, when the number of branches of the hydrophilic block side is 2, two molecular chains containing a polysarcosine chain may extend as branches from one N atom present in the linker site of a molecular chain containing a polylactic acid chain. In other words, an N atom directly or indirectly bound to a polylactic acid chain may be directly or indirectly bound to two polysarcosine chains.

Further, for example, when the number of branches of the hydrophilic block side is 3, three molecular chains containing a polysarcosine chain may extend as branches from one C atom present in the linker site of a molecular chain containing a polylactic acid chain. In other words, a C atom directly or indirectly bound to a polylactic acid chain may be directly or indirectly bound to three polysarcosine chains. The same applies when branching occurs at one P or Si atom present in the linker site, or when the whole molecule of the amphiphilic block polymer forms a quaternary ammonium molecule.

When the number of branches of the hydrophilic block side exceeds 3, the hydrophilic block side can be molecularly-designed so that the branches further have a branched structure.

When the hydrophobic block side is also branched, the hydrophobic block side can be molecularly-designed from the same viewpoint as described above.

A preferred structure of the branched-type amphiphilic block polymer in which the number of branches of the hydrophilic block side is 3 and the hydrophobic block side is not branched is represented by the following formula (I).

[Chemical formula 2]

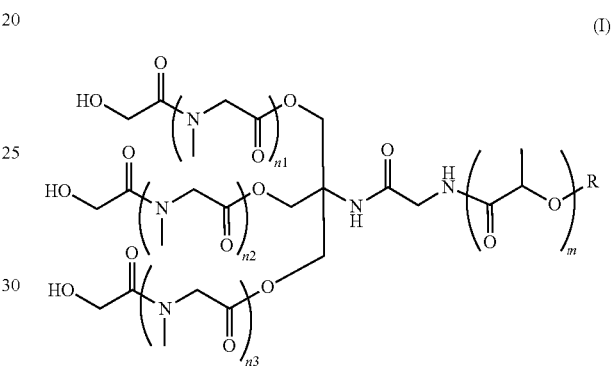

(I)

In the formula (I), n1, n2 and n3 represent numbers whose sum is 3 to 200, m represents a number of 5 to 100, and R represents a hydrogen atom or an organic group. The number of carbon atoms in the organic group may be 1 to 20. Specific examples of the organic group include alkyl groups, alkylcarbonyl groups, and the like.

A preferred structure of the branched-type amphiphilic block polymer in which the number of branches of the hydrophilic block side is 3 and the number of branches of the hydrophobic block side is 2 is represented by the following formula (II).

[Chemical formula 3]

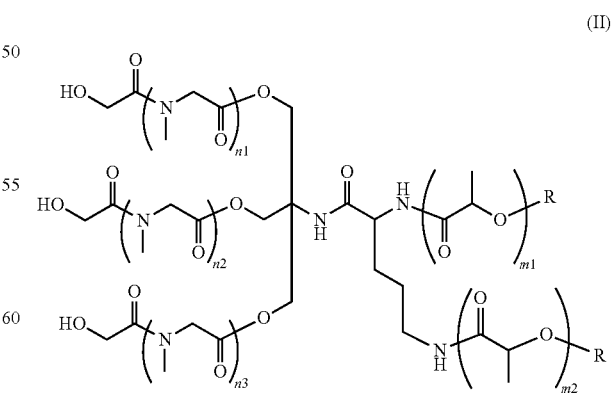

(II)

In the formula (II), n1, n2 and n3 and R are the same as those in the formula (I) and m1 and m2 represent numbers whose sum is 10 to 400.

[1-5. Synthesis Method of Branched-Type Amphiphilic Block Polymer]

In the synthesis of the branched-type amphiphilic block polymer, the synthesis of a hydrophobic block part (polylactic acid part), the synthesis of a hydrophilic block part (sarcosine part or polysarcosine part), and the synthesis of a linker part that links these blocks together are performed.

The branched-type amphiphilic block polymer can be synthesized by, for example, synthesizing a linker reagent that links sarcosine or polysarcosine chains and a polylactic acid chain(s) together, and then using the linker reagent as an initiator to perform attachment of a sarcosine site or extension of a polysarcosine site by polymerization reaction and extension of a polylactic acid site by polymerization reaction.

Further, the branched-type amphiphilic block polymer can be synthesized by, for example, extending a polylactic acid chain(s) after attachment of sarcosine to a linker reagent, or after attachment of polysarcosine chains, previously prepared as a hydrophilic block by polymerization reaction, to a linker reagent.

Furthermore, the branched-type amphiphilic block, polymer can be synthesized by, for example, previously preparing both sarcosine or polysarcosine chains and polylactic acid chains as a hydrophilic block and a hydrophobic block, respectively, and linking these blocks together using a linker reagent separately synthesized.

The linker reagent can have a structure in which the number of functional groups (e.g., hydroxyl groups, amino groups or the like) that can be bound to a lactic acid monomer (lactic acid or lactide) or a polylactic acid chain is one or equal to the desired number of branches of the hydrophobic block side and the number of functional groups (e.g., amino groups) that can be bound to a sarcosine monomer (e.g., sarcosine or N-carboxysarcosine anhydride) or polysarcosine is equal to the desired number of branches of the hydrophilic block side. In this case, the linker reagent is appropriately molecularly-designed by those skilled in the art so that each of the functional groups that can be bound to a sarcosine monomer or polysarcosine has the same reactivity as much as possible.

The functional group that can be bound to a lactic acid monomer or a polylactic acid chain and the functional group that can be bound to a sarcosine monomer or polysarcosine may each be protected with a protective group. In this case, as their respective protective groups, those that can be selectively removed if necessary are appropriately selected by those skilled in the art.

For example, a linker reagent used to synthesize the branched-type amphiphilic block polymer whose number of branches of the hydrophilic block side is 3 can be prepared based on, for example, a 2,2,2-triethanolamine (Tris) structure.

Further, in the case of allowing the hydrophobic block side to be branched, a linker reagent can be prepared based on, for example, a structure having a larger number of branching points than the 2,2,2-triethanolamine structure. The structure having a larger number of branching points can be obtained in the following manner: a derivative of amino acid (specific examples thereof include lysine and ornithine) having, in its side chain, an amino group as an example of a functional group that can be bound to a polylactic acid chain, in which all the amino groups are protected, is attached to 2,2,2-triethanolamine, and then deprotection is performed. The number of branching points can be increased by further attaching such an amino acid derivative to free amino groups obtained by deprotection.

A method for synthesizing the polysarcosine chain or the polylactic acid chain can be appropriately determined by those skilled in the art depending on the kind of functional group in a linker reagent, and may be selected from known peptide synthesis methods or polyester synthesis methods.

Peptide synthesis is preferably performed by, for example, ring-opening polymerization of N-carboxysarcosine anhydride (sarcosine NCA) using, as an initiator, a basic group, such as an amino group, in a linker reagent.

Polyester synthesis is preferably performed by, for example, ring-opening polymerization of lactide using, as an initiator, a basic group, such as an amino group, in a linker reagent.

When a branched-type amphiphilic block polymer different in the number of branches from the above specific example is synthesized, the branched-type amphiphilic block polymer can be prepared by those skilled in the art with appropriately making various changes in terms of organic chemistry.

The chain length of the polysarcosine chain or the polylactic acid chain can be adjusted by adjusting a loading ratio between the initiator and the monomer in the polymerization reaction. The chain length can be also determined by, for example, $^1$HNMR.

[2. Molecular Assembly]

A molecular assembly (lactosome) according to the present invention is a structure formed by aggregation or self-assembling orientation of the branched-type amphiphilic block polymer described above. The molecular assembly according to the present invention is preferably a micelle constituted to have a hydrophobic block on the inside (core) and a hydrophilic block on the outside in terms of practical use. The molecular assembly according to the present invention includes one composed of the branched-type amphiphilic block polymer (single type), and one composed of the branched-type amphiphilic block polymer and a linear type amphiphilic block polymer (mixed type).

Further, the molecular assembly according to the present invention is allowed to have an appropriate functional structure so as to be a useful structure as a probe for molecular imaging or a preparation for a drug delivery system.

[2-1. Single-Type Molecular Assembly Composed of Branched-Type Amphiphilic Block Polymer]

The branched-type amphiphilic block polymer is larger in the molecular cross-sectional area of a hydrophilic site than a linear amphiphilic block polymer due to the presence of a plurality of polysarcosine chains as branched chains. Therefore, the molecular assembly composed of the branched-type amphiphilic block polymer is excellent in stability as a particle. Further, such a particle can have a large curvature. Therefore, as will be described later, the molecular assembly according to the present invention has a basic characteristic that said molecular assembly can have a reduced particle size.

Further, the molecular assembly composed of the branched-type amphiphilic block polymer has a basic characteristic that said molecular assembly has a higher hydrophilic group density on the surface than conventional lactosomes due to the presence of a plurality of polysarcosine chains as branched chains, and therefore hydrophobic site in said molecular assembly is less exposed.

[2-2. Mixed-Type Molecular Assembly Composed of Branched-Type Amphiphilic Block Polymer and Linear Type Amphiphilic Block Polymer]

A linear type amphiphilic block polymer mixed with the branched-type amphiphilic block polymer in the molecular assembly according to the present invention may be an amphiphilic block polymer that has been used as a component of conventional lactosomes or an amphiphilic block polymer that has not been able to function as a component of conventional lactosomes. It is to be noted that the amphiphilic block polymer that has been used as a component of conventional lactosomes is a polymer that can self-assemble by itself to form a particle. Specifically, it is a polymer that has, when the number of sarcosine units is defined as $N^S$ and the number of polylactic acid units is defined as $N^L$, a ratio of $N^S/N^L$ of, for example, 1.8 or more (the upper limit within the range is not particularly limited but is, for example 5 or 4). On the other hand, the amphiphilic block polymer that has not been able to function as a component of conventional lactosomes is a polymer that exhibits amphiphilicity as a whole molecule of a copolymer composed of a hydrophilic block and a hydrophobic block but cannot self-assemble by itself to form a particle. Specifically, it is a polymer that has a ratio of $N^S/N^L$ of, for example, less than 1.8, for example 1.7 or less or 1.67 or less (the lower limit within the range is not particularly limited but is, for example, 0.05 or 0.1).

The linear type amphiphilic block polymer used in the present invention may be molecularly-designed from the same viewpoint as the branched-type amphiphilic block polymer according to the present invention except that it basically has a linear structure. Specifically, the linear type amphiphilic block polymer used may be one composed of a hydrophilic block containing one sarcosine or one polysarcosine chain and a hydrophobic block containing one polylactic acid chain. The number of sarcosine units in the hydrophilic block is, for example, 1 to 200, 1 to 29, 30 to 200, or 50 to 100. The number of lactic acid units in the hydrophobic block is, for example, 5 to 100, 15 to 60, or 25 to 45.

The mixed-type molecular assembly (branched/linear mixed-type molecular assembly) according to the present invention has the above-described basic characteristics of the single-type molecular assembly (branched single-type molecular assembly) according to the present invention, and in addition, due to the presence of the linear type amphiphilic block polymer mixed, can have a particle size intermediate between the particle size of the branched single-type molecular assembly according to the present invention and the particle size of a conventional lactosome (linear type single-type molecular assembly).

It is to be noted that in the case of the mixed-type molecular assembly, the branched-type amphiphilic block polymer and the linear amphiphilic block polymer are preferably the same in the optical activity of the polylactic acid chain to each other in terms of particle size control. For example, when the polylactic acid chain of the branched-type amphiphilic block polymer is composed of only L-lactic acid units, the polylactic acid chain of the linear type amphiphilic block polymer is also preferably composed of only L-lactic acid units.

In the case of the mixed-type molecular assembly, the mixing ratio between the branched-type amphiphilic block polymer and the linear type amphiphilic block polymer may be 50:50 to 100:0, and preferably 67:33 to 100:0 on molar basis. If the proportion of the linear type amphiphilic block polymer exceeds the above range, it tends to be difficult to obtain the effects of the present invention obtained by the branched-type amphiphilic block polymer.

[2-3. Particle Size]

The particle size of the molecular assembly according to the present invention may be, for example, 10 to 50 nm. The upper limit within the range may be 35 nm, 30 nm, 25 nm, or 20 nm. The term "particle size" used herein refers to a particle size occurring most frequently in particle size distribution, that is, a mode particle size. As has been described above, the molecular assembly according to the present invention basically tends to have a smaller particle size than conventional ones due to the branched structure of the hydrophilic block of the amphiphilic block polymer.

The single-type molecular assembly tends to have a relatively small particle size within the above range. Specifically, the single-type molecular assembly may have a particle size of, for example, 10 to 35 nm. The upper limit within the range may be 30 nm, 25 nm, or 20 nm.

On the other hand, the mixed-type molecular assembly tends to have a relatively large particle size. Specifically, the mixed-type molecular assembly may have a particle size of, for example, 20 to 50 nm. The lower limit within the range may be 25 nm, 30 nm, 25 nm, 30 nm, or 35 nm, and the upper limit may be 35 nm.

In either case, a molecular assembly having a particle size smaller than the lower limit of the above range can be obtained by shortening the chain length of the branched-type amphiphilic block polymer. If the particle size exceeds the above range, it is difficult to obtain a preferred EPR effect when the molecular assembly is administered as a molecular probe into a living body, which tends to make short-term imaging difficult.

Examples of a method for controlling the particle size include a method in which the chain length of the polymer constituting the molecular assembly is shortened to adjust the particle size to be smaller; a method in which the amount of the linear type amphiphilic block polymer to be blended is reduced to adjust the particle size to be smaller; a method in which the amount of an encapsulated substance is reduced to adjust the particle size to be smaller; and the like.

A method for measuring the size of the molecular assembly according to the present invention is not particularly limited, and is appropriately selected by those skilled in the art. Examples of such a method include an observational method with a TEM (Transmission Electron Microscope) and a DLS (Dynamic Light Scattering) method. In the case of a DLS method, the translational diffusion coefficient of particles undergoing Brownian movement in a solution is measured.

[2-4. Embodiment Having Functional Structure]

The molecular assembly according to the present invention can have a functional structure that allows the molecular assembly to have a useful form or function for use in a molecular imaging system or a drug delivery system. Therefore, the molecular assembly according to the present invention can be a structure useful as a probe for molecular imaging or a preparation for a drug delivery system.

Examples of a specific embodiment of the molecular assembly having a functional structure include an embodiment in which a functional group selected from the group consisting of a signal group and a ligand group is bound to the amphiphilic block polymer itself constituting the molecular assembly, and an embodiment in which the molecular assembly encapsulates a functional substance selected from the group consisting of a signal agent and a drug.

[2-4-1. Binding of Functional Group]

The functional group is, for example, an organic group, and is appropriately selected by those skilled in the art depending on the intended use of the molecular assembly. Examples of the functional group include a signal group and a ligand group.

A signal group is a group having a property detectable for imaging. Examples of such a signal group include fluorescent groups, radioactive element-containing groups, and magnetic groups. Means for detecting these groups may be appropriately selected by those skilled in the art.

Examples of the fluorescent groups include, but are not limited to, groups derived from fluorescein-based dyes, cyanine-based dyes such as indocyanine dyes, rhodamine-based dyes, and quantum dots.

In the present invention, near-infrared fluorescent groups (e.g., groups derived from cyanine-based dyes or quantum dots) are preferably used.

Each substituent group having a hydrogen bond exhibits absorption in the near-infrared region (700 to 1300 nm), but the degree of absorption is relatively small. Therefore, near-infrared light easily penetrates through living tissue. It can be said that by utilizing such characteristics of near-infrared light, in-vivo information can be obtained without putting an unnecessary load on the body. Particularly, when a target to be measured is decided to a site close to the body surface of a small animal, near-infrared fluorescence can give useful information.

More specific examples of the near-infrared fluorescent groups include groups derived from indocyanine dyes such as ICG (indocyanine green), Cy7, DY776, DY750, Alexa790, Alexa750, and the like. In a case where the molecular assembly according to the present invention is intended for use targeting, for example, cancer, groups derived from an indocyanine dye such as ICG may be particularly preferably used from the viewpoint of accumulation in a cancer.

Examples of the radioactive element-containing groups include, but are not limited to, groups derived from saccharides, amino acids, or nucleic acids labeled with a radioisotope such as $^{18}F$. One specific example of a method for introducing a radioactive element-containing group includes a method comprising the step of polymerizing lactide using mono-Fmoc (9-fluorenylmethyloxycarbonyl)ethylenediamine, the step of protecting a terminal OH group by a silyl protecting group, the step of eliminating Fmoc by piperidine treatment, the step of polymerizing sarcosine-N-carboxyanhydride (SarNCA) and terminating the end of the polymer, the step of eliminating the silyl protecting group to perform conversion to a sulfonate ester (e.g., trifluoromethanesulfonate ester, p-toluenesulfonate ester), and the step of introducing a radioactive element-containing group. If necessary, this specific example may be modified by those skilled in the art.

Examples of the magnetic groups include, but are not limited to, groups having a magnetic substance such as ferrichrome and groups contained in ferrite nanoparticles and magnetic nanoparticles.

The ligand group shall be one that binds to a biomolecule expressed in a target cell to control the directivity of the molecular assembly to thereby improve the targeting property of the molecular assembly. Examples of the ligand group include an antibody, a cell-adhesive peptide, a sugar chain, a water-soluble polymer, and the like.

Examples of the antibody include those having an ability to specifically bind to an antigen expressed in a cell in a target site.

Examples of the cell-adhesive peptide include adhesion factors such as RGD (arginine-glycine-aspartic acid).

Examples of the sugar chain include stabilizers such as carboxymethyl cellulose and amylose, and those having an ability to specifically bind to a protein expressed in a cell in a target site.

Examples of the water-soluble polymer include polymers such as polyether chains and polyvinyl alcohol chains.

Such a group can be preferably bound to the terminal structural unit of the hydrophilic block-side in the amphiphilic block polymer. This makes it possible, when a micelle is formed, to obtain a particle having the functional groups on its surface, that is, a particle having a surface modified with the functional groups.

[2-4-2. Encapsulation of Functional Substance]

The functional substance is selected from the group consisting of a signal agent and a drug. This substance is a hydrophobic compound and is encapsulated by placing said substance in the hydrophobic core of the molecular assembly.

As the signal agent, a molecule having the above-described signal group can be used. Among such molecules, near-infrared fluorescent substances such as indocyanine green-based dyes, or radioactive element-containing substances such as saccharides, amino acids, or nucleic acids labeled with a radioisotope such as $^{18}F$ may be preferably used in the present invention.

As the drug, one suitable for a target disease is appropriately selected by those skilled in the art. Specific examples of the drug include anticancer drugs, antimicrobial agents, antiviral agents, anti-inflammatory agents, immunosuppressive drugs, steroid drugs, hormone drugs, anti-angiogenic agents, and the like. These drug molecules may be used singly or in combination of two or more thereof.

The functional substance to be encapsulated may be bound with a polylactic acid group.

The polylactic acid group is a group comprising lactic acid units as a main component. All the lactic acid units may be either continuous or discontinuous. The structure, chain length, and optical purity of the polylactic acid group can be basically determined from the same viewpoint as described above with reference to the molecular design of the hydrophobic block. This also makes it possible to obtain the effect that the functional substance can have excellent affinity for the hydrophobic block of the amphiphilic block polymer in the molecular assembly.

The number of lactic acid units of the polylactic acid group is 15 to 60, and preferably 25 to 45. Within the above range, the polylactic acid-bound functional substance is molecularly-designed so that its entire length does not exceed the length of the above-described amphiphilic block polymer. Preferably, the polylactic acid-bound functional substance is molecularly-designed so that its entire length does not exceed twice the length of the hydrophobic block of the amphiphilic block polymer. If the number of structural units exceeds the above range, when a molecular assembly is formed, the resultant molecular assembly tends to lack stability. If the number of structural units is less than the above range, the affinity of the functional substance for the hydrophobic block of the amphiphilic block polymer tends to be lowered.

It is to be noted that the polylactic acid chain of the polylactic acid-bound functional substance is preferably the same in optical activity as that of the branched-type amphiphilic block polymer or the linear type amphiphilic block polymer as the component of the molecular assembly. For example, when the polylactic acid chain of the branched-type amphiphilic block polymer or the linear type amphiphilic block polymer is composed of L-lactic acid units, it is preferred that the polylactic acid chain of the polylactic acid-bound functional substance is also composed of L-lactic acid units.

The amount of the functional substance encapsulated is not particularly limited, but when the functional substance is, for example, a fluorescent substance, the amount of a fluorescent dye may be 0.5 to 50 mol %, for example, 0.5 to 1 mol % or 1 to 50 mol % with respect to the total amount of the amphiphilic block polymer and the fluorescent dye. The same can be applies to the amount of another functional substance (a radioactive substance as an example) encapsulated.

[2-5. Formation of Molecular Assembly]

A method for forming the molecular assembly is not particularly limited, and can be appropriately selected by those skilled in the art depending on, for example, the desired size and characteristics of the molecular assembly and the kind, properties, and amount of a functional structure to be carried by the molecular assembly. If necessary, after being formed by a method that will be described later, the resultant molecular assemblies may be surface-modified by a known method.

It is to be noted that whether particles have been formed or not may be confirmed by observation with an electron microscope.

[2-5-1. Film Method]

The branched-amphiphilic block polymer according to the present invention is soluble in low-boiling point solvents, and therefore the molecular assembly can be prepared by a film method.

The film method includes the following steps of: preparing a solution, in a container (e.g., a glass container), containing the branched-type amphiphilic block polymer in an organic solvent (e.g., a solution containing the branched-type amphiphilic block polymer and the functional substance in an organic solvent); removing the organic solvent from the solution to obtain a film comprising the branched-type amphiphilic block polymer (e.g., a film comprising the branched-type amphiphilic block polymer and the functional substance) on an inner wall of the container; and adding water or an aqueous solution into the container and performing ultrasonic treatment or warming treatment to convert the film-like substance into a molecular assembly (e.g., a molecular assembly encapsulating the functional substance), thereby obtaining a dispersion liquid of the molecular assembly. The film method may further include the step of subjecting the dispersion liquid of the molecular assembly to freeze-drying treatment.

The solution containing the branched-type amphiphilic block polymer and the functional substance in an organic solvent may be prepared by previously preparing a film comprising only the branched-type amphiphilic block polymer, and then adding a solution containing the functional substance to the film for dissolution at the time of nanoparticle preparation.

In the case of preparation of the mixed-type molecular assembly, the respective steps described above shall be performed in a state where the linear type amphiphilic block polymer is mixed with the branched-type amphiphilic block polymer.

Preferred examples of the organic solvent used in the film method include low-boiling point solvents. In the present invention, the term "low-boiling point solvent" refers to one whose boiling point is 100° C. or less, and preferably 90° C. or less at 1 atmospheric pressure. Specific examples of such a low-boiling point solvent include chloroform, diethyl ether, acetonitrile, ethanol, acetone, dichloromethane, tetrahydrofuran, hexane, and the like.

The use of such a low-boiling point solvent makes it very easy to perform solvent removal. A method for solvent removal is not particularly limited, and may be appropriately determined by those skilled in the art depending on the boiling point of an organic solvent to be used, or the like. For example, solvent removal may be performed under reduced pressure or by natural drying.

After the organic solvent is removed, a film containing the branched-type amphiphilic block polymer is formed on the inner wall of the container. Water or an aqueous solution is added to the container to which the film is attached. The water or aqueous solution is not particularly limited, and biochemically or pharmaceutically acceptable ones may be appropriately selected by those skilled in the art. Examples thereof include distilled water for injection, normal saline, a buffered solution, and the like.

After water or an aqueous solution is added, warming treatment is performed. The film is peeled off from the inner wall of the container by warming, and in this process, the molecular assembly is formed. The warming treatment can be performed under conditions of, for example, 70 to 100° C. and 5 to 60 minutes. After the completion of the warming treatment, a dispersion liquid in which the molecular assembly (when the functional substance is used, the molecular assembly encapsulating the functional substance) is dispersed in the water or aqueous solution is prepared in the container. Further, if necessary, ultrasonic treatment may be performed in combination when the film is peeled off.

The obtained dispersion liquid can be directly administered to a living body. That is, the molecular assembly does not need to be stored by itself under solvent-free conditions.

On the other hand, the obtained dispersion liquid may be subjected to freeze-drying treatment. A method for freeze-drying treatment is not particularly limited, and any known method can be used. For example, the dispersion liquid of the molecular assembly obtained in such a manner as described above may be frozen by liquid nitrogen and sublimated under reduced pressure. In this way, a freeze-dried product of the molecular assembly is obtained. That is, the molecular assembly can be stored as a freeze-dried product. If necessary, water or an aqueous solution may be added to the freeze-dried product to obtain a dispersion liquid of the molecular assembly, and the molecular assembly can be used. The water or aqueous solution is not particularly limited, and biochemically or pharmaceutically acceptable ones may be appropriately selected by those skilled in the art. Examples thereof include distilled water for injection, normal saline, a buffer solution, and the like.

[2-5-2. Injection Method]

An injection method includes the following steps: preparing a solution, in a container (e.g., a test tube), containing the branched-type amphiphilic block polymer in an organic solvent; dispersing the solution in water or an aqueous solution; and removing the organic solvent. In the injection method, the step of purification treatment may be appropriately performed before the step of removing the organic solvent.

Examples of the organic solvent used in the injection method include trifluoroethanol, ethanol, hexafluoroisopropanol, dimethylsulfoxide, dimethylformamide, and the like.

Examples of the water or aqueous solution used include distilled water for injection, normal saline, a buffer solution and the like.

Examples of the purification treatment performed include gel filtration chromatography, filtering, ultracentrifugation, and the like.

[3. Drug Delivery System and Molecular Imaging]

[3-1. Object to which Molecular Assembly is to be Administered]

A drug delivery system and molecular imaging according to the present invention include administration of the above-described molecular assembly to a living body. The living body to which the molecular assembly is administered is not particularly limited, but may be a human or a non-human animal. The non-human animal is not particularly limited, and may be a mammal other than a human. Specific examples thereof include primates, gnawing mammals (e.g., mice, rats), rabbits, dogs, cats, pigs, bovines, sheep, horses, and the like.

The molecular assembly used in the method according to the present invention is excellent in specific accumulation in a vascular lesion site (e.g., a malignant tumor site, an inflammatory site, an arterial sclerosis site, an angiogenic site). The molecular assembly according to the present invention accumulates in the tissue of such a site due to EPR (enhanced permeability and retention) effect, and therefore its accumulation does not depend on the kind of tissue of a vascular lesion site. The administration target of the fluorescent probe according to the present invention is preferably a cancer. Examples of the cancer as the administration target include a wide variety of cancers such as liver cancers, pancreas cancers, lung cancers, uterine cervical cancers, breast cancers, and colon cancers.

[3-2. Administration]

A method for administration to a living body is not particularly limited, and can be appropriately determined by those skilled in the art. Therefore, the administration method may be either systemic or local. That is, the molecular probes can be administered by any one of injection (needle injection or needleless injection), oral administration, and external administration.

The molecular assembly according to the present invention has a dense polymer brush structure of sarcosine chains in its particle surface due to the branched structure of the branched-type amphiphilic block polymer as its essential component. Therefore, it is considered that, as compared to conventional lactosomes, the hydrophobic site of the particle is less exposed to an external environment, and therefore the recognition of the particle as a foreign substance by the external environment is suppressed. The molecular assembly according to the present invention makes it possible to achieve a reduction in ABC phenomenon believed to be due to this matter. Therefore, the molecular assembly according to the present invention can be administered more than once. For example, the molecular assemblies according to the present invention may be administered to the same individual two or more necessary times (e.g., 2 to 10 times). Further, the span between administrations may be, for example, 1 to 60 days.

[3-3. Detection of Molecular Assembly]

The molecular imaging according to the present invention includes the step of detecting signals derived from the administered molecular assembly. By detecting the administered molecular assembly, it is possible to observe the appearances of an administration target (especially, the position and size of cancer tissue, and the like) from outside the body.

As a detection method, any means that can visualize the administered molecular assembly can be used. The detection means can be appropriately determined by those skilled in the art depending on the kind of signal group or signal substance of the molecular assembly.

When the particle size of the molecular assembly is the same as that of a molecular assembly by a conventional method, the time from administration to the start of detection can be appropriately determined by those skilled in the art depending on the kind of functional structure of the molecular assembly to be administered and the kind of administration target. For example, detection may be started after a lapse of 1 to 24 hours from administration. If the time is shorter than the above range, a detected signal is too strong, and therefore it tends to be difficult to clearly distinguish an administration target from other sites (background). On the other hand, if the time is longer than the above range, the molecular assembly tends to be excreted from the administration target.

On the other hand, the molecular assembly according to the present invention is excellent in stability as a particle due to the branched structure of the branched-type amphiphilic block polymer as its essential component, and a molecular assembly with a small particle size, which is not previously attainable, can be prepared. When the molecular assembly having a small particle size is administered to a living body, the rate of accumulation of the molecular assembly in target tissue by the EPR effect can be accelerated, and excretion of the molecular assembly to the outside of the body by the kidney can be accelerated. Therefore, when the molecular assembly is smaller in particle size than those by a conventional method, the time from administration to the start of detection can be shortened as compared to a conventional method. For example, the time may be 1 to 24 hours, and preferably 1 to 9 hours. The present invention makes it possible to reduce the particle size of a molecular assembly, and therefore the ratio of contrast at tumor site to background can be increased in a short period of time after intravascular administration so that short-time selective imaging of a cancer site can be achieved.

It is to be noted that from the viewpoint of accuracy, detection of the molecular assembly is preferably performed by measuring a living body not from one direction but from two or more directions. Specifically, a living body may be measured from at least three directions, and more preferably from at least five directions. When measurement is performed from five directions, a living body can be measured from, for example, both right and left abdomen sides, both right and left sides of the body, and a back side.

EXAMPLES

Hereinbelow, the present invention will be described in more detail with reference to examples, but is not limited thereto.

Example 1

Synthesis of Branched-Type Amphiphilic Block Polymer (1)

In this example, a branched-type amphiphilic block polymer, in which three polysarcosine (PS) chains were bound to one polylactic acid (L-polylactic acid: PLLA) chain, was synthesized.

[Chemical formula 4]

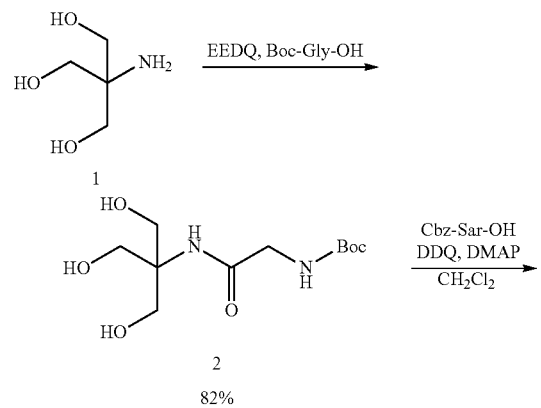

-continued

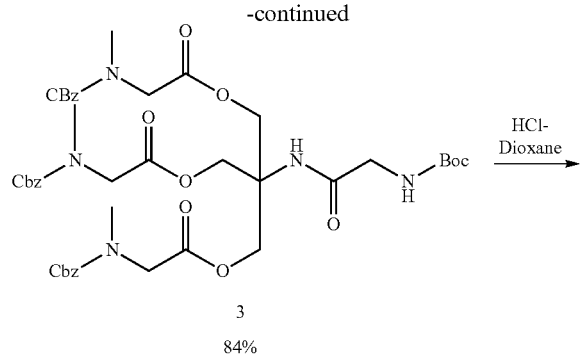

3
84%

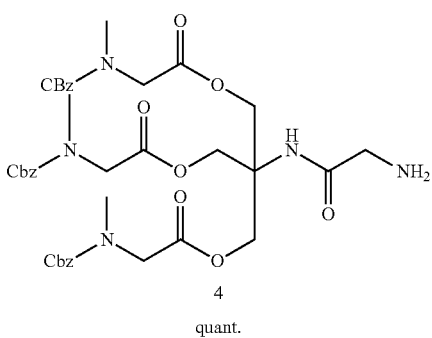

4
quant.

As an outline, first, a linker reagent was synthesized. The linker reagent was synthesized from tris hydroxymethyl aminomethane (Tris) 1 having one amino group as an initiator of PLLA polymerization and three hydroxyl groups as an initiator of NCA (N-carboxy anhydride) polymerization in a sarcosine site. Further, appropriate protective groups were attached to the amino group and hydroxyl groups of Tris 1 so that these groups could be deprotected, if necessary. Specifically, the amino group of Tris 1 was protected with a protective group having a Boc group by using N-tert-butoxycarbonylglycine (Boc-Gly-OH) in the presence of 2-ethoxy-1-ethoxycarbonyl-1,2-dihydroquinoline (EEDQ) to obtain a compound 2, and further the hydroxyl groups of the compound 2 were protected with protective groups having a Cbz group by using benzyloxycarbonylsarcosine (Cbz-Sar-OH) in the presence of dichlorodicyanobenzoquinone (DDQ) and dimethylaminopyridine (DMAP) to obtain a compound 3 as a linker reagent. Only the Boc group of the linker reagent 3 was selectively removed for deprotection using HCl-Dioxane to obtain an amino group-containing compound 4.

A specific synthesis procedure is as follows.

[Compound 2]

Boc-glycine (2.5 g, 0.014 mol) and EEDQ (6.0 g, 0.024 mol) were added to an EtOH solution (75 mL) containing tris(hydroxymethyl)aminomethane (1.9 g, 0.016 mol) and stirred under reflux (95° C.) for 4.5 hours. After the completion of reaction, a precipitate was removed with filter paper, EtOH was distilled away under reduced pressure, and then purification was performed by silica gel column chromatography (CHCl$_3$/MeOH mixtures with mixing ratios (v/v) of 1/0, 40/1, and 10/1 were used as eluents in this order). The thus obtained product 2 had a weight of 3.2 g (0.012 mol), and a yield of 82% was achieved.

[Compound 3]

To a mixture of the compound 2 (278 mg, 1.0 mmol), Cbz-Sar-OH (804 mg, 3.6 mmol), DCC (887 mg, 4.3 mmol), and DMAP (26 mg, 0.21 mmol) was added 10 mL of dichloromethane cooled with ice, and then the resultant mixture was stirred at room temperature overnight. After the completion of reaction, washing with ethyl acetate was performed, a white precipitate (urea) was removed, and then purification was performed by silica gel chromatography (n-hexane/ethyl acetate mixtures with mixing ratios (v/v) of 2/1, 1/1, and 1/2 were used as eluents in this order). As a result, a target compound 3 (719 mg) was obtained in a yield of 84%.

[Compound 4]

To the compound 3 (710 mg) cooled with ice was added 4 mol/L HCl/Dioxane (7.0 mL) for dissolution to obtain a reaction solution, and the reaction solution was stirred at room temperature for 5 minutes. Then, the solvent was distilled away from the reaction solution under reduced pressure, and purification was performed by silica gel chromatography (a CHCl$_3$/MeOH mixture with a mixing ratio of 10/0 (v/v) was used as an eluent).

The thus obtained white precipitate was dissolved in chloroform to obtain a solution, and the solution was subjected to phase separation by adding an aqueous 1N NaOH solution to remove an HCl salt from a terminal amino group. Then, the solution was dehydrated with anhydrous magnesium sulfate, and the magnesium sulfate was removed by Celite filtration to obtain a compound 4.

[Chemical formula 5]

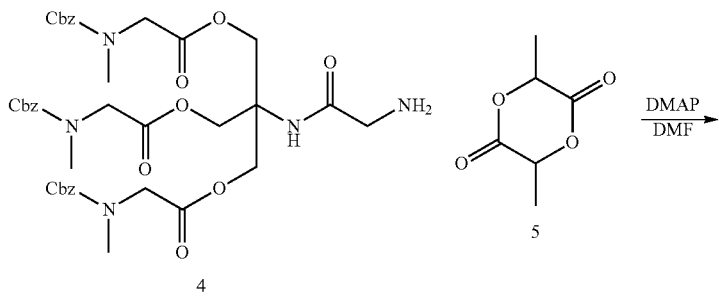

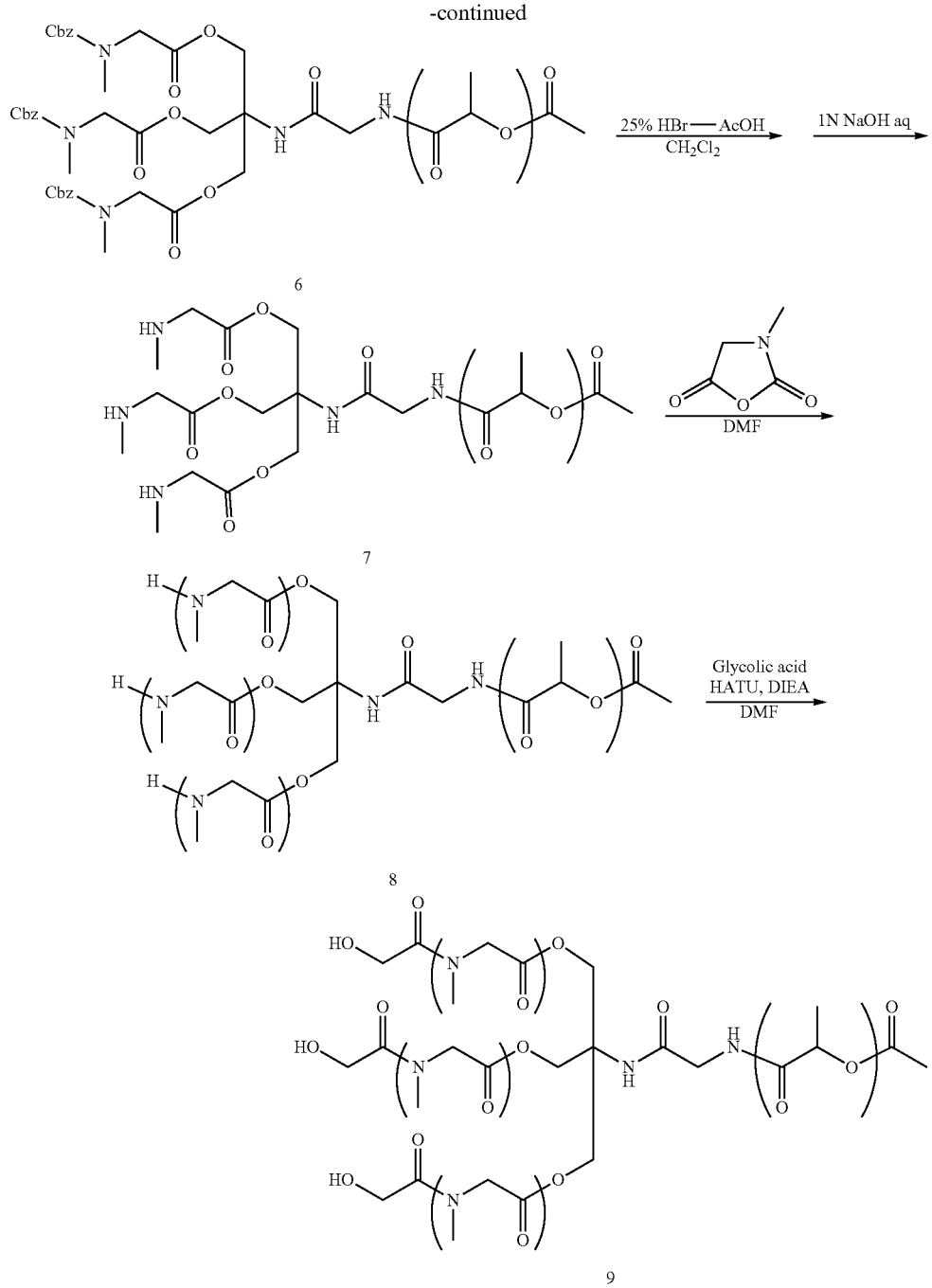

Then, lactide 5 was subjected to a polymerization reaction using the amino group-containing compound 4 as an initiator to synthesize a PLLA chain so that a compound 6 was obtained. The Cbz groups remaining as protective groups in the compound 6 were removed with HBr—AcOH for deprotection, and at the same time, the terminal hydroxyl group of PLLA was protected with an acetyl group. Sarcosine-NCA was subjected to N-carboxyanhydride polymerization reaction using three amino groups in a compound 7 as an initiator to synthesize PS chains so that a compound 8 is obtained. Further, glycolic acid, O-(benzotriazol-1-yl)-N,N,N',N'-tetramethyluroniumhexafluorophosphate (HATU), and N,N-diisopropylethylamine (DIEA) were added to the compound 8 to introduce carboxyl groups thereinto so that a branched-type amphiphilic block polymer 9 is obtained. It is to be noted that in the above formula, numbers representing the degree of polymerization are omitted.

A specific synthesis procedure is as follows.

[Compound 6]

To a DMF solution (2 mL) containing the initiator 4 (485 mg, 0.61 mmol) dissolved therein were added 15 equivalents (1.32 g, 9.2 mmol) of L-lactide (5) relative to the initiator 4 and DMAP (75 mg, 0.61 mmol), and then the resultant mixture was stirred at 55° C. in an argon atmosphere overnight (for about 15 hours). The reaction solvent DMF was removed to some extent by distillation under reduced pressure to obtain a concentrate, and the concentrate was then dropped into cold MeOH. The thus obtained white precipitate was collected by centrifugation to obtain a compound 6.

[Compound 7]

The compound 6 was dissolved in 10 mL of dichloromethane to obtain a reaction solution, and the reaction solution was cooled to 0° C., and then 20 mL of 25% HBr—AcOH was added thereto. The reaction solution was stirred at room temperature overnight, and then the solvent was distilled away under reduced pressure so that a white precipitate was obtained. The white precipitate was subjected to NMR measurement, and as a result, it was confirmed that removal of Cbz groups for deprotection had been completed.

The obtained white precipitate was dissolved in chloroform to obtain a solution, and the solution was subjected to phase separation by adding an aqueous 1N NaOH solution to remove an HBr salt from terminal amino groups. Successively, the solution was dehydrated with anhydrous magnesium sulfate, and the magnesium sulfate was removed by Celite filtration to obtain a compound 7.

[Compounds 8 and 9]

A polymerization reaction was performed using the compound 7 as a macroinitiator to form a hydrophilic site. Sar-NCA was added to a DMF solution of the compound 7 in an amount of 40 or 60 equivalents relative to the initiator, and then the concentration of Sar-NCA was adjusted to 0.50 M. The thus obtained reaction solution was stirred at room temperature for 24 hours to obtain a compound 8, and then glycolic acid, HATU, and DIEA were added thereto, and further stirred for 24 hours. After the completion of reaction, the reaction solution was concentrated and then purified by size exclusion chromatography (Sephadex LH20, eluent: DMF) to obtain a target amphiphilic block polymer 9.

The $^1$H NMR measurement result of the obtained amphiphilic block polymer 9 is shown in FIG. 1. From result shown in FIG. 1, the composition of the branched-type amphiphilic block polymer obtained in this example was identified, and it was found that the number of lactic acid units in the PLLA chain was 30 and the number of sarcosine units per one PS chain was 34.

Example 2

Preparation of Branched Single-Type Molecular Assembly (Preparation of Molecular Assembly from Only Branched-Type Amphiphilic Block Polymer) (1)

In this example, a molecular assembly (polymeric micelle; lactosome) was prepared by a film method from the branched-type amphiphilic block polymer 9 obtained in Example 1.

1.0 mg of the branched-type amphiphilic block polymer 9 was dissolved in an appropriate amount of chloroform, and then the solvent was distilled away under reduced pressure to form a polymer film on a wall of a test tube. The polymer film was vacuum-dried overnight to sufficiently remove chloroform, and then 1.0 mL of normal saline was added to the film and was subjected to ultrasonic treatment in a bath sonicator filled with water at 85° C. for 5 minutes to prepare a dispersion liquid of a molecular assembly.

The obtained dispersion liquid was observed by dynamic light scattering (DLS) and with a transmission electron microscope (TEM).

Figure 2:
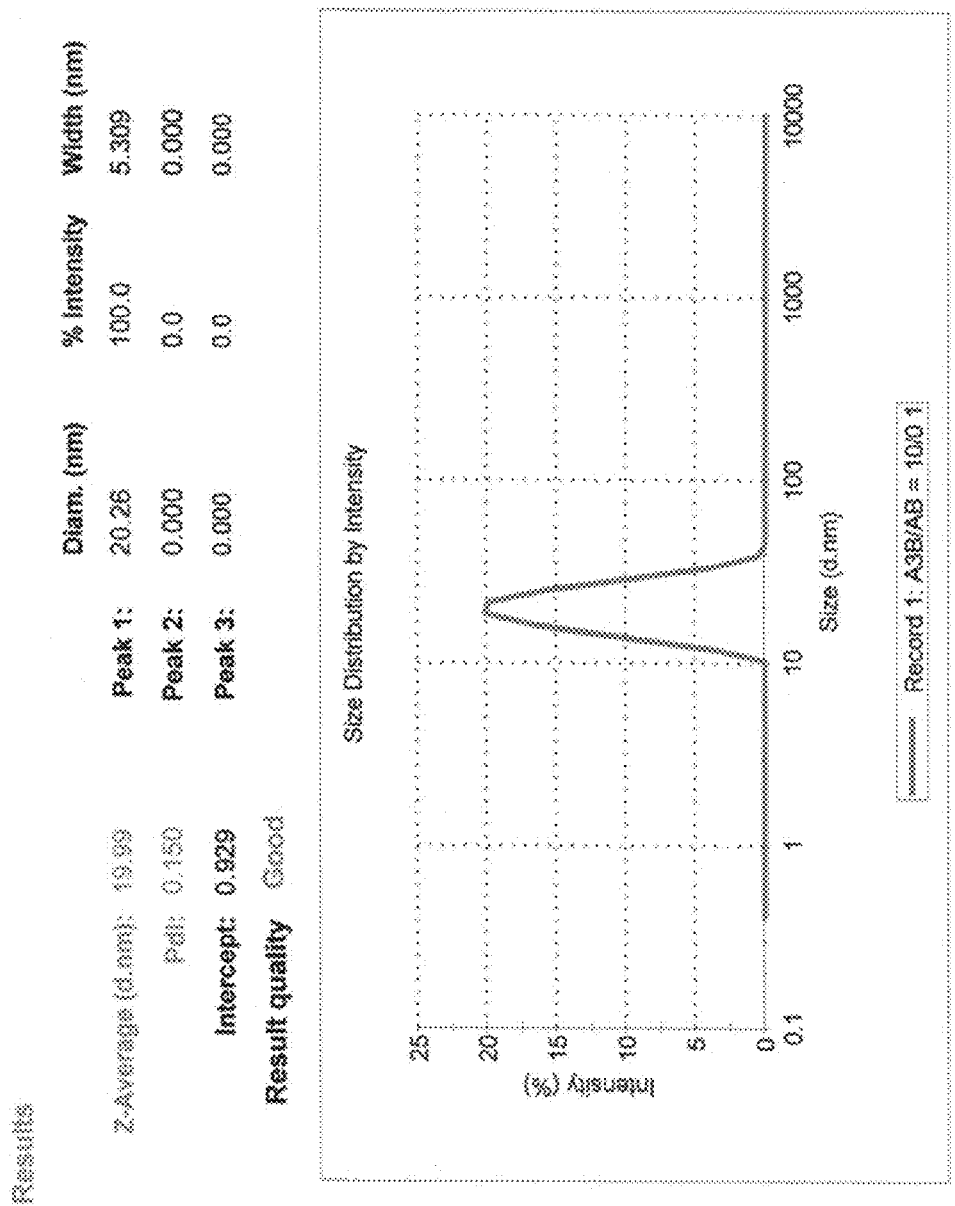
FIG. 2 shows the results of DLS measurement of a branched single-type molecular assembly (polymeric micelles; lactosomes) prepared in Example 2 and composed of only a branched-type amphiphilic block polymer.

The results of the DLS measurement are shown in FIG. 2. From a size distribution chart shown in FIG. 2, the dispersion liquid prepared from the branched-type amphiphilic block polymer exhibited a monodisperse peak whose peak top particle size (Diam.) was 20.26 nm, Z-average value (Z-average) was 19.99 nm, and peak width (Width) was 5.309 nm.

Figure 3:
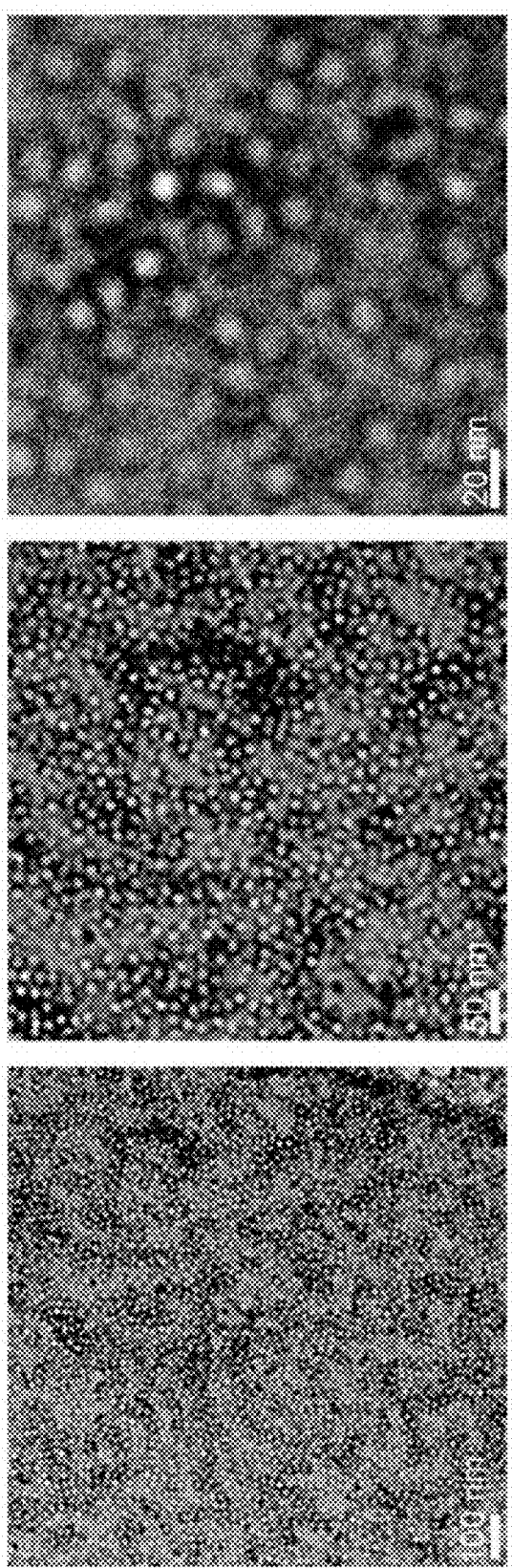
FIG. 3 shows the TEM images of the branched single-type molecular assembly prepared in Example 2 and composed of only a branched-type amphiphilic block polymer.

The results of the TEM observation are shown in FIG. 3. In FIG. 3, three kinds of photographs different in scale are shown. As shown in FIG. 3, it was confirmed that polymeric micelles having a particle size as small as about 20 nm (lactosomes with small particle size) were obtained.

Comparative Example 1

Synthesis of Linear Type Amphiphilic Block Polymer and Linear Single-Type Molecular Assembly Prepared Therefrom (1)

A linear type amphiphilic block polymer was synthesized, in which one polysarcosine (PS) chain was bound to one polylactic acid (L-polylactic acid; PLLA) chain.

Synthesis of Aminated Poly-L-Lactic Acid (a-PLA)

Aminated poly-L-lactic acid (a-PLA) was synthesized using L-lactide (11) and N-carbobenzoxy-1,2-diaminoethane hydrochloride (12).

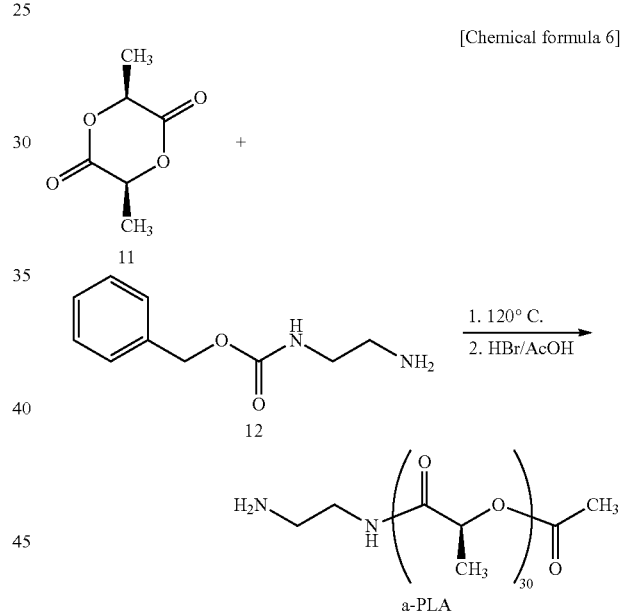

[Chemical formula 6]

To N-carbobenzoxy-1,2-diaminoethane hydrochloride (12) (310 mg, 1.60 mmol) as a polymerization initiator was added toluene (1.0 mL) in which tin octanoate (6.91 mg) was dispersed. Then, the toluene was distilled away under reduced pressure, and then L-lactide (11) (3.45 g, 24 mmol) was added to perform a polymerization reaction at 120° C. in an Ar atmosphere. After 12 hours, the reaction container was air-cooled to room temperature. The obtained yellowish white solid was dissolved in a small amount of chloroform (about 10 mL). The chloroform was dropped into cold methanol (100 mL) to obtain a white precipitate. The obtained white precipitate was collected by centrifugation and dried under reduced pressure.

To a dichloromethane solution (1 mL) of the obtained white precipitate (500 mg) was added 25 v/v % hydrogen bromide/acetic acid (2.0 mL) to obtain a reaction solution, and the reaction solution was protected from light and stirred for 2 hours in dry air. After the completion of reaction, the reaction solution was dropped into cold methanol (100 mL), and then a deposited precipitate was collected by centrifugation. The obtained white precipitate was dissolved in chloroform, and then washed with a saturated aqueous NaHCO$_3$ solution and dehydrated with anhydrous MgSO$_4$. The MgSO$_4$ was removed by Celite (registered trademark) filtration, and then the resultant product was subjected to vacuum drying to obtain a white amorphous powder of a-PLA (440 mg).

Synthesis of Polysarcosine-Poly-L-Lactic Acid (PSL1)

An amphiphilic substance, polysarcosine-poly-L-lactic acid (PSL1) was synthesized from sarcosine-NCA (Sar-NCA) and aminated poly-L-lactic acid (a-PLA).

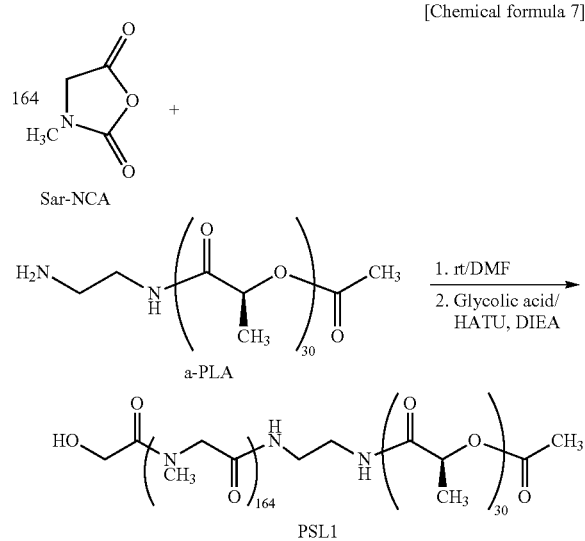

Dimethylformamide (DMF) (140 mL) was added to a-PLA (383 mg, 0.17 mmol) and sarcosine-NCA (Sar-NCA) (3.21 g, 27.9 mmol) in an Ar atmosphere to obtain a reaction solution, and the reaction solution was stirred at room temperature for 12 hours. The reaction solution was cooled to 0° C., and then glycolic acid (72 mg, 0.95 mmol), O-(benzotriazol-1-yl)-N,N,N',N'-tetramethyluroniumhexafluorophosphate (HATU) (357 mg, 0.94 mmol), and N,N-diisopropylethylamine (DIEA) (245 µL, 1.4 mmol) were added thereto and allowed to react at room temperature for 18 hours.

After DMF was distilled away under reduced pressure by a rotary evaporator, purification was performed using an LH20 column. Fractions showing a peak detected at UV 270 nm were collected and concentrated. The thus obtained concentrated solution was dropped into diethyl ether at 0° C. for reprepicitation to obtain a target substance, PSL1 (1.7 g).

Synthesis of Sarcosine-Poly(Leucine-Aminoisobutyric Acid) (SLA)

An amphiphilic substance, sarcosine-poly(leucine-aminoisobutyric acid) (SLA) was synthesized from sarcosine-NCA (Sar-NCA) and poly(leucine-aminoisobutyric acid) (LAI).

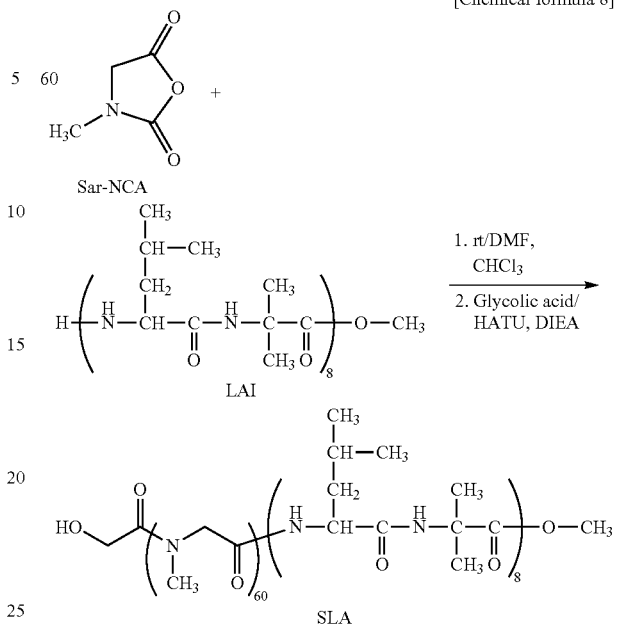

Boc-(Leu-Aib)$_8$-OMe (600 mg, 0.349 mmol) was added to a mixed solution of 6.0 mL of trifluoroacetic acid (TFA) and 0.6 mL of anisole so that a Boc group was removed and a TFA salt derivative was obtained. The TFA salt derivative was washed with isopropyl ether and dried under vacuum for 2 hours. The residue was dissolved in chloroform and neutralized with a 4 wt % aqueous sodium hydrogen carbonate solution to remove a TFA group. The chloroform solution was concentrated to obtain 420 mg (0.259 mmol) of poly(leucine-aminoisobutyric acid) (LAI) (H-(Leu-Aib)$_8$-OMe; LAI).

The obtained LAI was dissolved in 8.0 mL of a 1/1 (v/v) mixed solution of DMF/HCl$_3$ to obtain a solution, and the solution was added to a solution obtained by dissolving Sar-NCA (1.11 g, 15.6 mmol) in 6.0 mL of a 1/1 (v/v) mixed solution of DMF/HCl$_3$ to obtain a reaction solution. After the Sar-NCA was consumed by reaction, the reaction solution was cooled to 0° C., and glycolic acid (98 mg, 1.30 mmol), HATU (492 mg, 1.30 mmol), and DIEA (338 µL, 1.94 mmol) were added thereto and stirred at room temperature for 10 hours. To the reaction solution, glycolic acid (40 mg, 0.52 mmol), HATU (198 mg, 0.52 mmol), and DIEA (135 µL, 0.78 mmol) were further added and stirred for 12 hours. After the completion of reaction, the reaction solution was concentrated and subjected to gel filtration using Sephadex LH-20 to purify a target substance, SLA (186 mg).

Preparation of Lactosome Nanoparticles Using Linear Type Polylactic Acid-Based Amphiphilic Block Polymer A chloroform solution of the linear type polylactic acid-based amphiphilic block polymer (0.2 mM) was prepared. Then, the solvent was distilled away under reduced pressure to form a film on a wall surface of a glass container. Further, the film was dispersed in water or a buffer solution in the glass container and was subjected to ultrasonic treatment at 60° C. for 30 minutes to obtain a dispersion liquid of a molecular assembly.

Further, the obtained dispersion liquid was frozen with liquid nitrogen and sublimated under reduced pressure to obtain a freeze-dried product. Water was added again to the obtained freeze-dried product to obtain a lactosome.

The molecular assembly composed of only the linear type amphiphilic block polymer had a particle size of 35 nm.

Example 3

Preparation of Branched/Linear Mixed-Type Molecular Assembly (Preparation of Molecular Assembly from Mixture of Branched-Type Amphiphilic Block Polymer and Linear Type Amphiphilic Block Polymer In this example, molecular assemblies (polymeric micelles; lactosomes) were prepared by a film method from a mixture of the branched-type amphiphilic block polymer obtained in Example 1 and the linear type amphiphilic block polymer obtained in Comparative Example 1.

The branched-type amphiphilic block polymer and the linear type amphiphilic block polymer were dissolved in an appropriate amount of chloroform in arbitrary ratios, and the same manner as in Example 2 was performed to prepare dispersion liquids of molecular assemblies. The dispersion liquids were subjected to DLS measurement and observed with a TEM.

Figure 4:
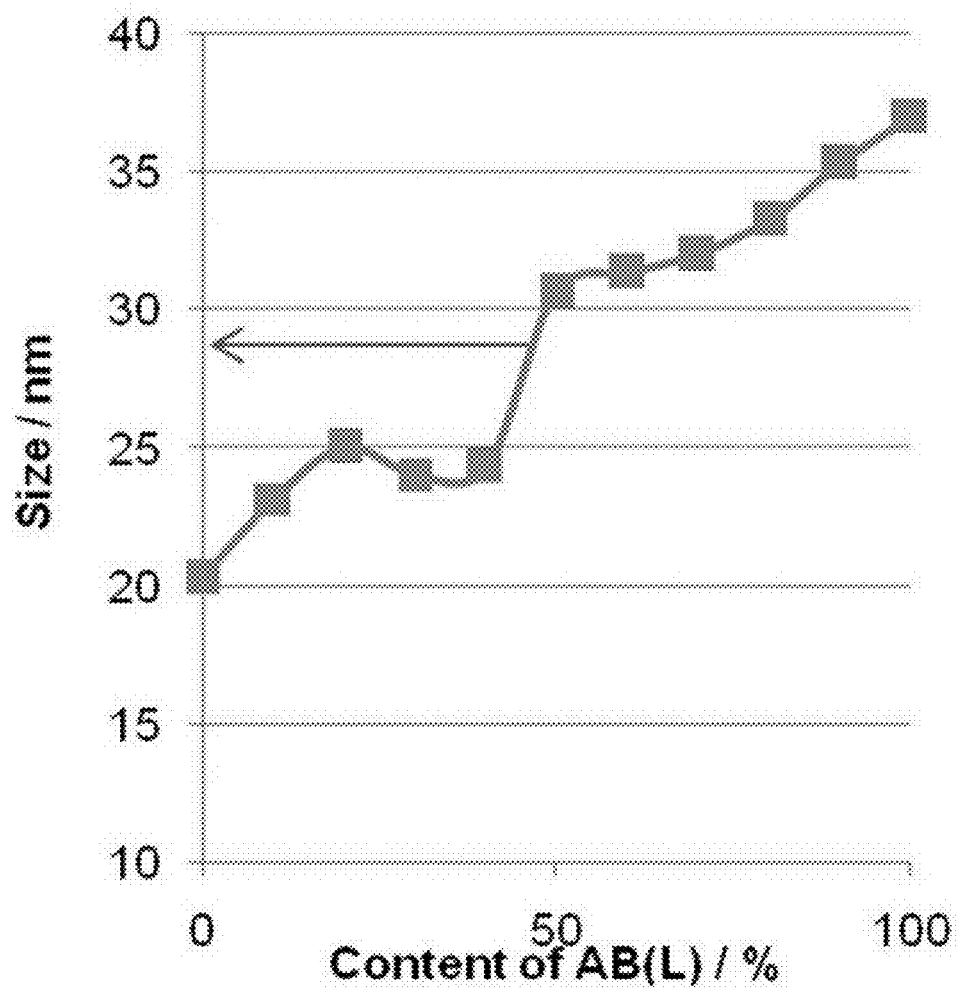
FIG. 4 shows the results of DLS measurement of branched/linear mixed-type molecular assemblies prepared in Example 3 and composed of a branched-type amphiphilic block polymer and a linear type amphiphilic block polymer.

FIG. 4 shows the results of the DLS measurement. In FIG. 4, the horizontal axis represents the content of linear type amphiphilic block polymer (Content of AB (L) %) and the vertical axis represents a particle size (Size/nm). From FIG. 4, it was confirmed that, as a result of the DLS measurement of the prepared dispersion liquids of molecular assemblies, the particle size was changed by changing the mixing ratio between the amphiphilic block polymers.

Figure 5:
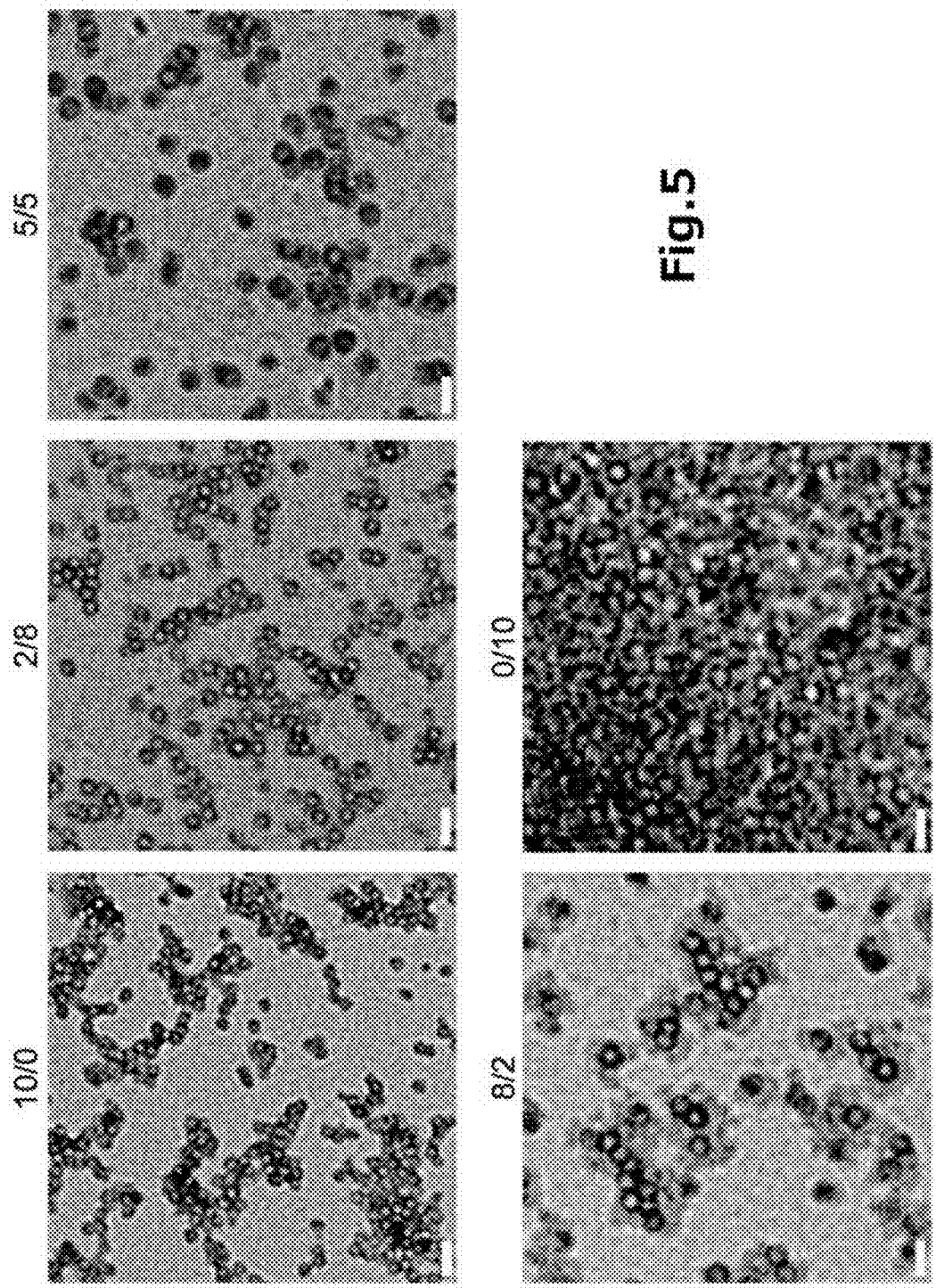
FIG. 5 shows the results of TEM observation of the branched/linear mixed-type molecular assemblies prepared in Example 3 and composed of a branched-type amphiphilic block polymer and a linear type amphiphilic block polymer.

FIG. 5 shows the results of the TEM observation. In FIG. 5, the mixing ratio is expressed as branched-type amphiphilic block polymer/linear type amphiphilic block polymer. From FIG. 5, it was confirmed that uniform polymeric micelles (lactosomes) different in particle size were formed by changing the mixing ratio between the amphiphilic block polymers.

The branched single-type molecular assembly prepared in Example 2 had a particle size of 20 nm, whereas the branched/linear mixed-type molecular assemblies prepared in this example had a particle size of 20 to 35 nm. On the other hand, as shown in Comparative Example 1, the linear single-type molecular assembly had a particle size of 35 nm. That is, this indicates that the branched/linear mixed-type molecular assemblies prepared in this example can have an arbitrary particle size between the particle size of the linear single-type molecular assembly and the particle size of the branched single-type molecular assembly.

Example 4

Evaluation of Disposition of ICG-Modified Branched Single-Type Molecular Assembly Synthesis of ICG-labeled poly-L-lactic acid (PLA-ICG)

The aminated poly-L-lactic acid (a-PLA) was labeled with ICG to obtain ICG-labeled poly-L-lactic acid (PLA-ICG). Specifically, a DMF solution containing 1 mg (1.3 eq) of an indocyanine green derivative (ICG-sulfo-OSu) dissolved therein was added to a DMF solution containing 1.9 mg (1.0 eq) of a-PLA and stirred at room temperature for about 20 hours. Then, the solvent was distilled away under reduced pressure, and purification was performed using an LH20 column to obtain a compound, PLA-ICG.

[Chemical formula 9]

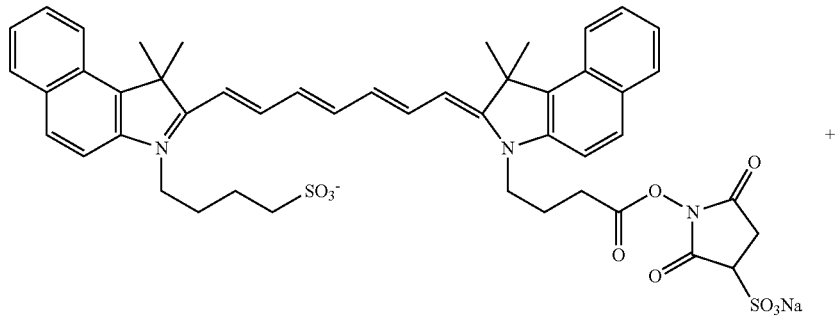

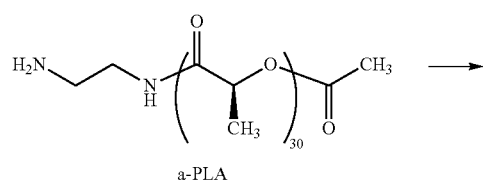

a-PLA

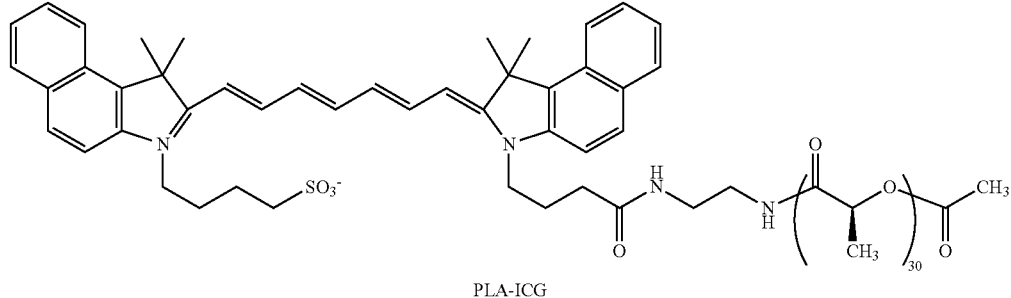

PLA-ICG

Preparation of ICG-Modified Branched Single-Type Molecular Assembly

A dispersion liquid of ICG-modified branched single-type molecular assembly was prepared in the same manner as in Example 2 except that 3 wt % of the ICG-labeled polylactic acid (ICG-PLLA) was further mixed with the chloroform solution of branched-type amphiphilic block polymer. In-vivo fluorescent imaging of a cancer-bearing mouse (right shoulder, subcutaneous implantation) was performed using the ICG-modified branched single-type molecular assembly obtained in this example.

For comparison, ICG-modified linear single-type molecular assembly was prepared in the same manner from the linear type amphiphilic block polymer synthesized in Comparative Example 1, and in-vivo fluorescent imaging was performed.

Figure 6:
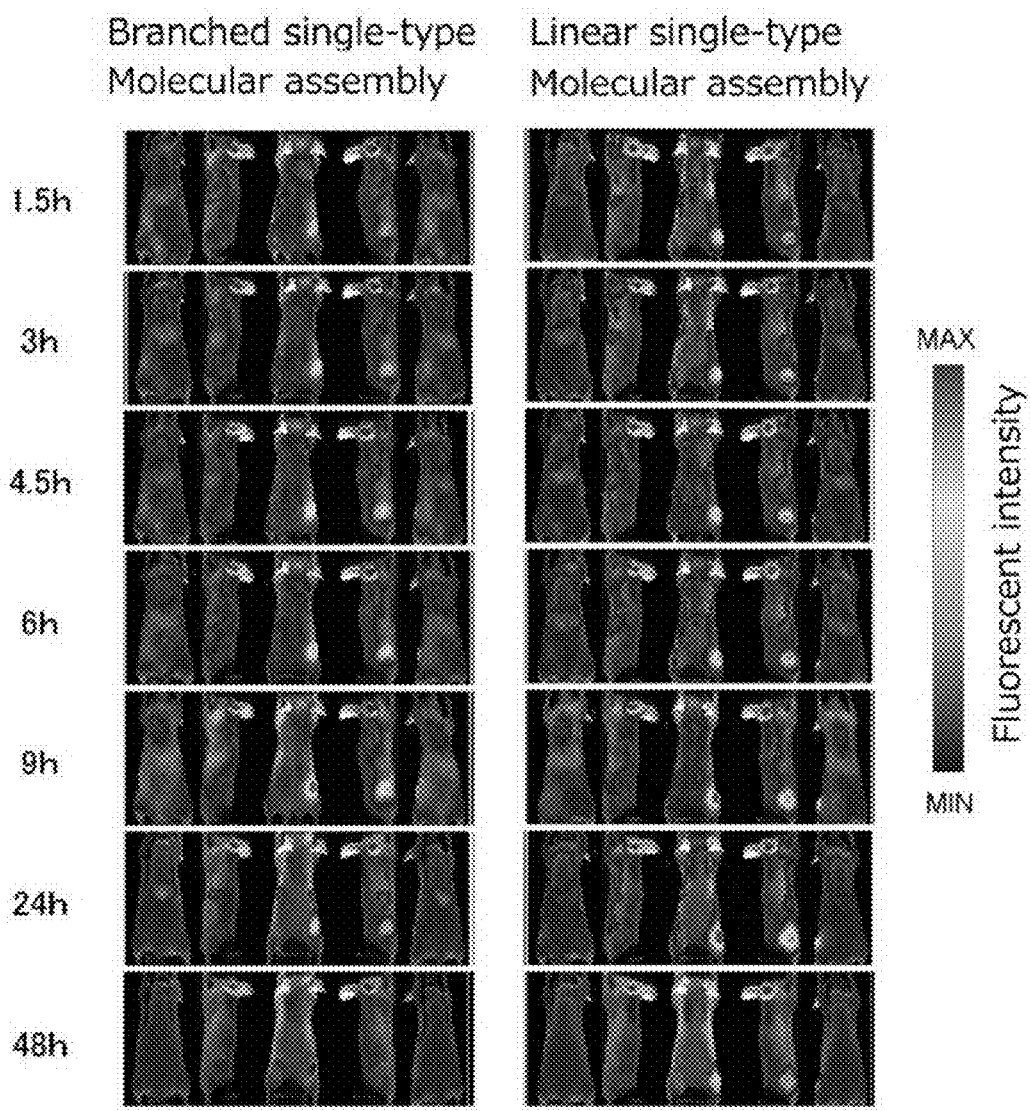
FIG. 6 shows the results of near-infrared imaging of a cancer-bearing mouse given ICG-modified branched single-type molecular assembly, which was obtained in Example 4.

FIG. 6 shows the results of the fluorescent imaging. It was confirmed that, as in the case of the linear single-type molecular assembly prepared for comparison, the branched single-type molecular assembly was less accumulated in the liver but accumulated in the tumor (right shoulder) by the EPR effect.

Figure 7:
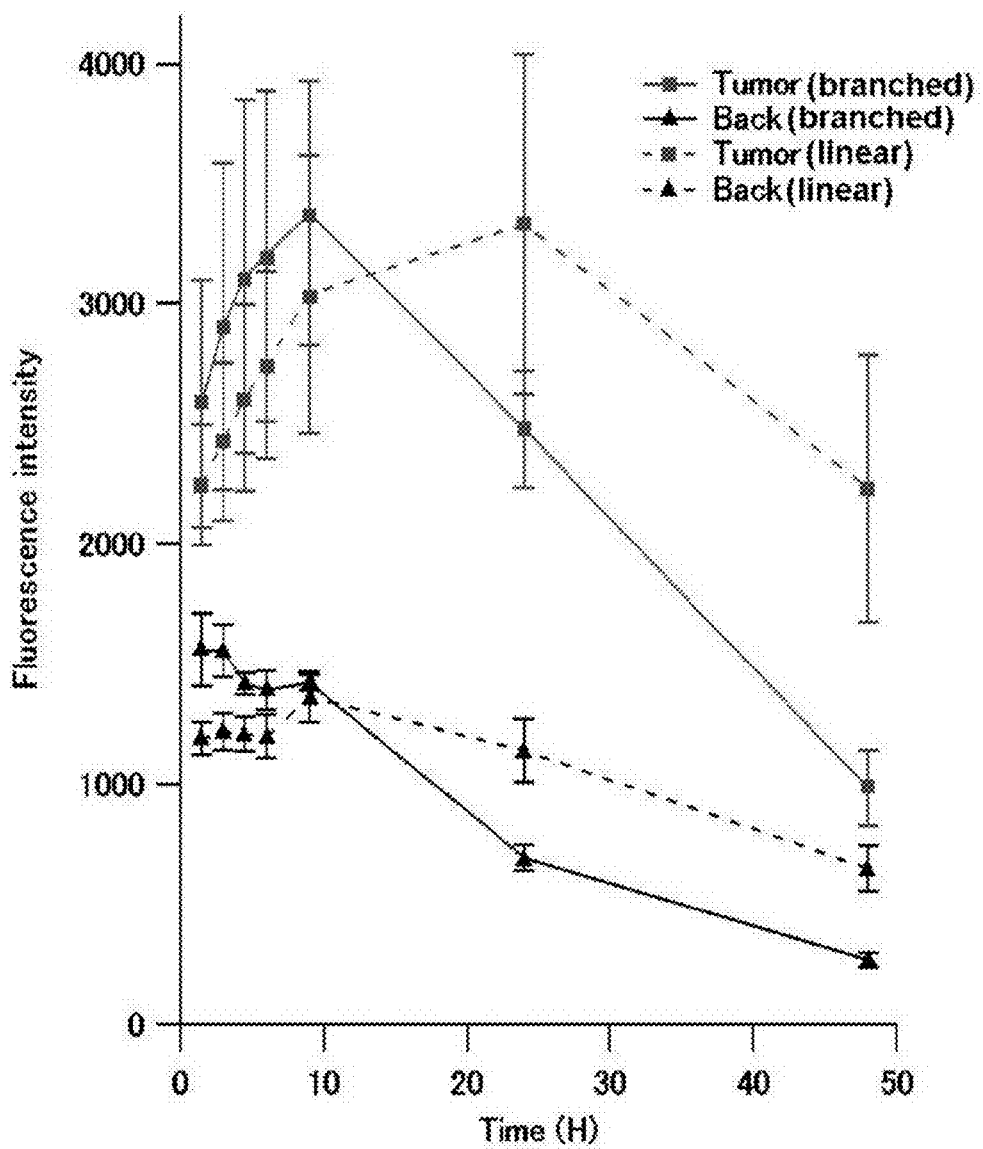
FIG. 7 shows changes in fluorescence intensity with time in the liver, background (back), and tumor of cancer-bearing mice given ICG-modified branched single-type molecular assembly in near-infrared imaging.

FIG. 7 shows changes in fluorescence intensity with time in the right shoulder tumor (Tumor) and back (Back). In FIG. 7, the vertical axis represents fluorescence intensity and the horizontal axis represents time (Time (H)). In the case of the linear type molecular assembly, the fluorescence intensity in the cancer site peaked about 24 hours after administration, but in the case of the branched-type lactosome, the fluorescence intensity in the cancer site peaked about 9 hours after administration. The changes in fluorescence intensity in the background and the cancer site, and the changes in the contrast with time between the cancer site and the background were evaluated, and as a result, in the case of the branched-type lactosome, the contrast was maximized after 6 hours. That is, it was confirmed that short-time imaging can be achieved by the molecular assembly according to the present invention.

Example 5

Evaluation of ABC Effect

In this example, 8 days after the administration performed in Example 4, the branched single-type molecular assemblies or the linear single-type molecular assembly (for comparison) was again administered to the mice, and in-vivo fluorescent imaging was performed. It is to be noted that two mice were used in each of a branched single-type molecular assembly administration group and a linear single-type molecular assembly administration group.

Figure 8:
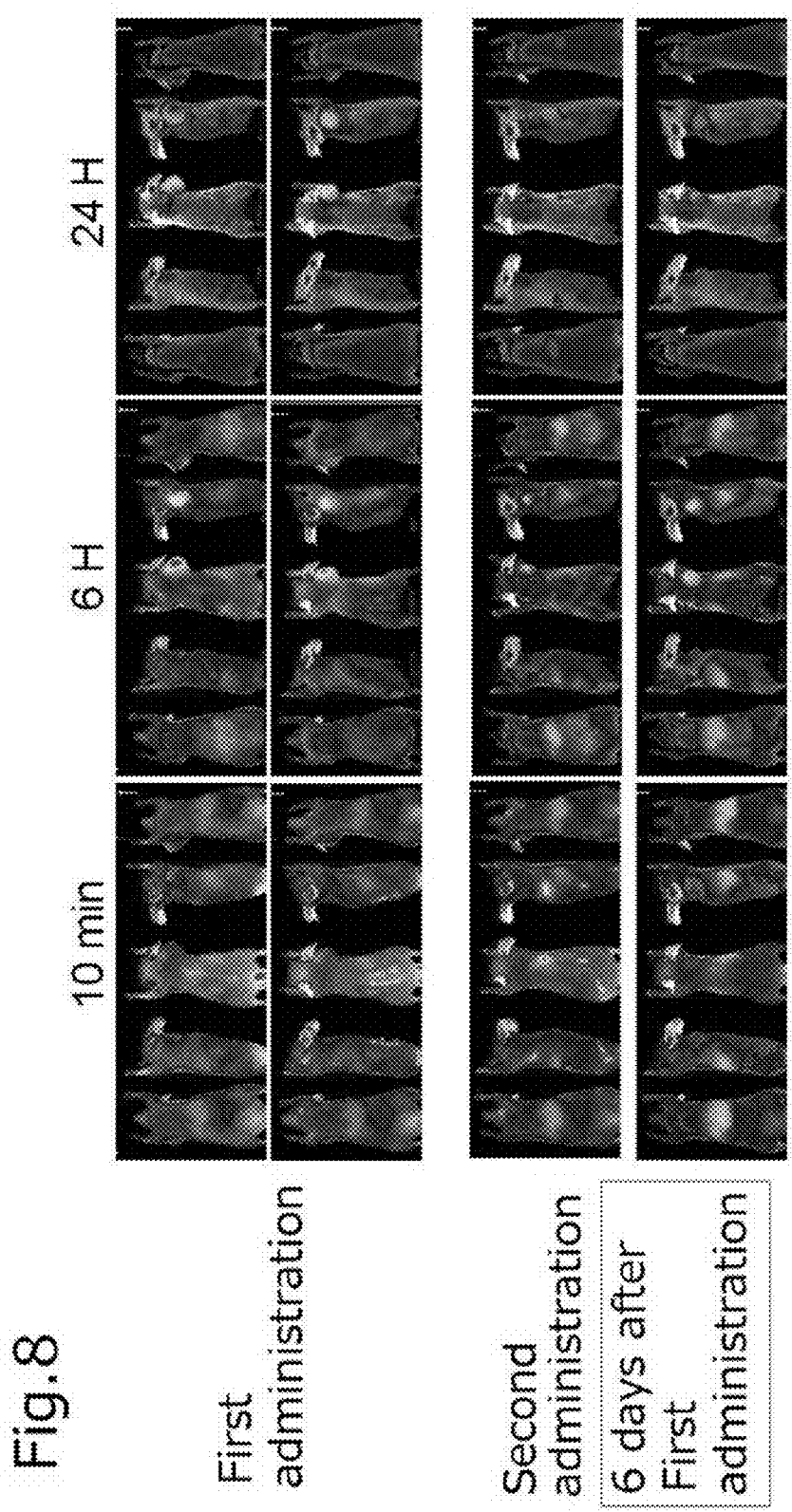
FIG. 8 shows the results of near-infrared imaging of cancer-bearing mice after readministration of branched single-type molecular assembly or linear single-type molecular assembly (for comparison), which were obtained in Example 5.
Figure 9:
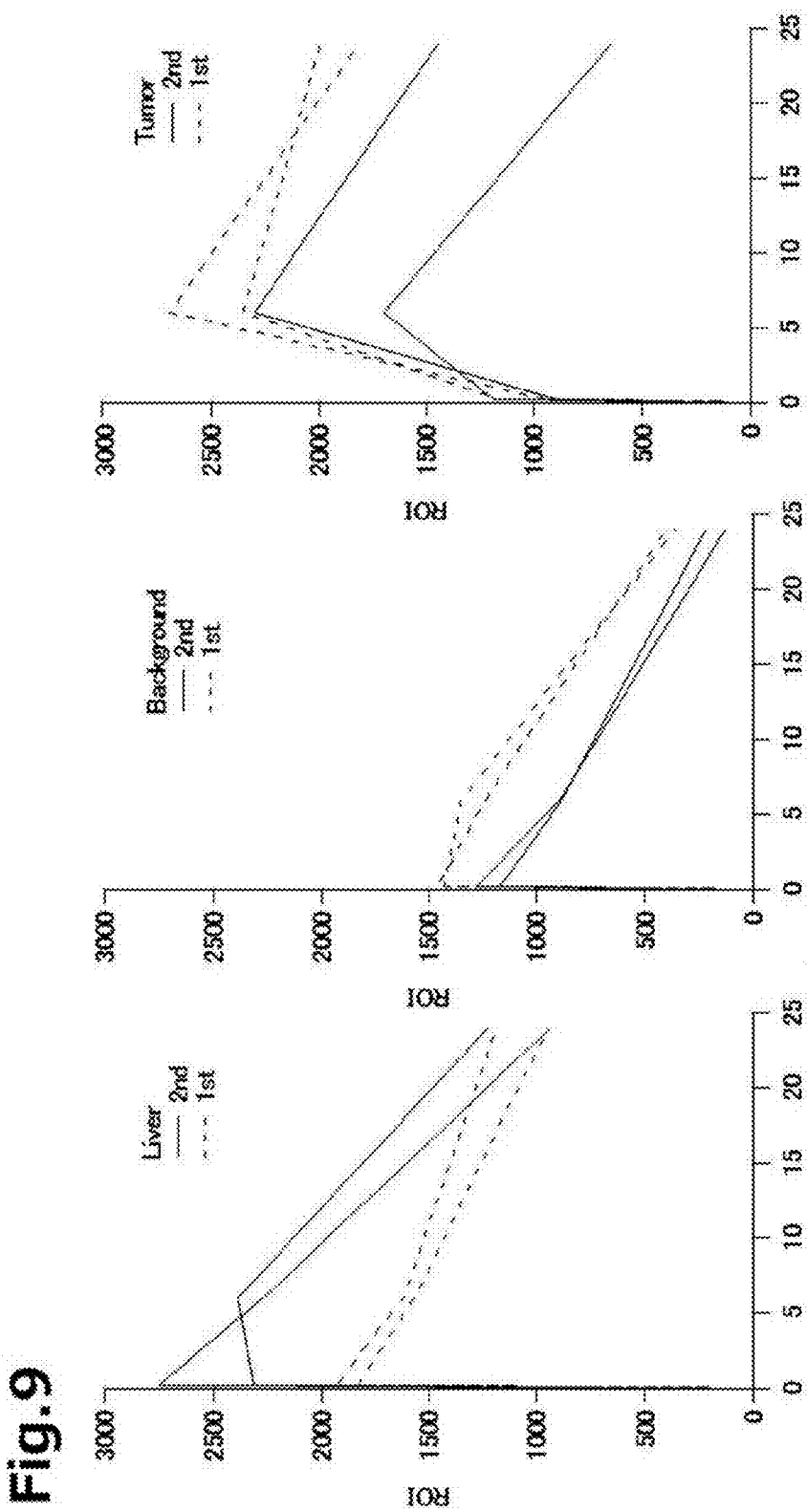
FIG. 9 shows changes in fluorescence intensity with time in the ROIs of the liver, background (back), and tumor of the cancer-bearing mice in near-infrared imaging after readministration of branched single-type molecular assembly or linear single-type molecular assembly (for comparison).

FIG. 8 shows the results of the fluorescent imaging as in FIG. 6. Further, FIG. 9 shows changes with time in the ROIs of the liver (Liver), back (Background), and right shoulder tumor (Tumor) after first administration (1st) and second administration (2nd).

In the case of the linear single-type molecular assembly (for comparison), almost all the amount of the molecular assembly were accumulated in the liver just after readministration (data not shown). On the other hand, in the case of the branched single-type molecular assembly, the amount of the molecular assembly accumulated in the liver was slightly increased just after readministration, but accumulation in the cancer site was observed after 6 hours. That is, it was confirmed that in the case of the branched single-type molecular assembly, sufficient fluorescence intensity for the fluorescent imaging of the tumor site was ensured. Therefore, it was apparent that the branched single-type molecular assembly can be administered more than once because inhibition of their accumulation in a tumor site due to the ABC effect is reduced.

Figure 10:
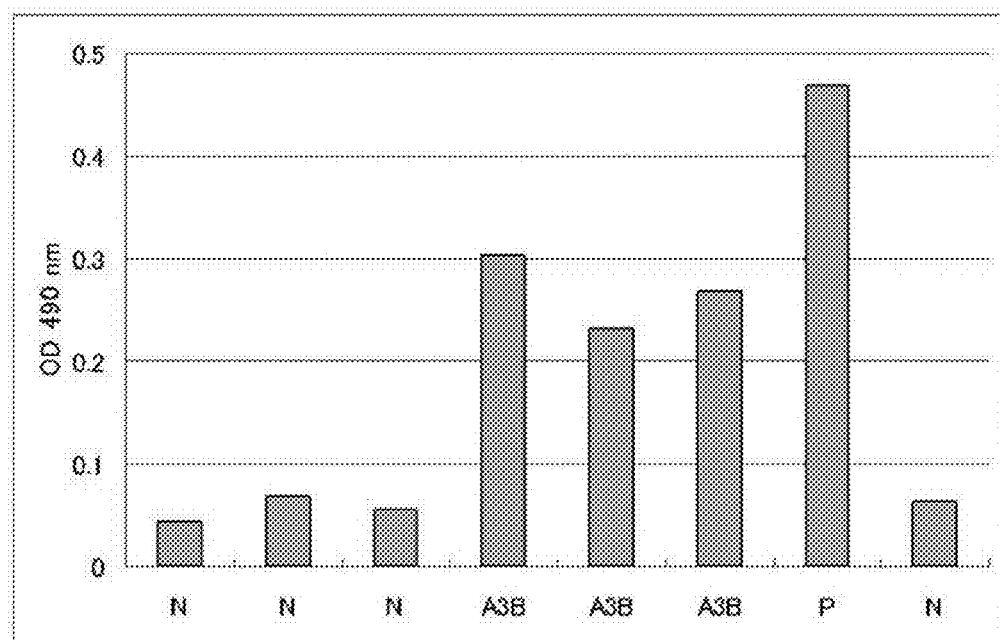
FIG. 10 shows the results of ELISA performed to determine the amounts of antibody in plasmas collected from mice one week after administration of branched single-type molecular assembly or linear single-type molecular assembly (for comparison).

FIG. 10 shows the results of ELISA performed to determine the amounts of antibody in plasmas collected from mice one week after administration of the branched single-type molecular assembly or the linear single-type molecular assembly (for comparison). In FIG. 10, N represents the results of control, A3B represents the results of the branched single-type molecular assembly, and P represents the result of the linear single-type molecular assembly (for comparison). As shown in FIG. 10, it was confirmed that the amount of antibody produced in the mouse administered with the branched single-type molecular assembly was reduced to about ½ to ⅔ of that in the mouse administered with the linear single-type molecular assembly. It is considered that such a smaller amount of antibody production contributed to the fact that the branched single-type molecular assembly was accumulated in the cancer without being trapped in the liver even after the second administration (i.e., to a reduction in the ABC effect).

Example 6

Synthesis of Branched-Type Amphiphilic Block Polymer (2)

In this example, a branched-type amphiphilic block polymer in which three polysarcosine chains were bound to one end of one polylactic acid chain was synthesized using a linker reagent different from that used in Example 1.

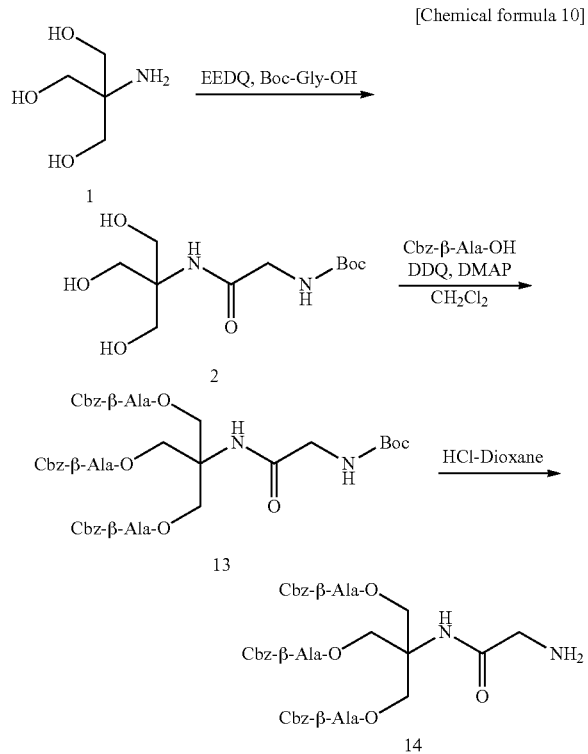

A compound 2 was synthesized in the same manner as in Example 1. A linker reagent 13 was obtained and then an amino group-containing compound 14 was obtained by selective deprotection in the same manner as in Example 1 except that benzyloxycarbonyl-β-alanine (Cbz-β-Ala-OH) was used instead of benzyloxycarbonylsarcosine (Cbz-Sar-OH).

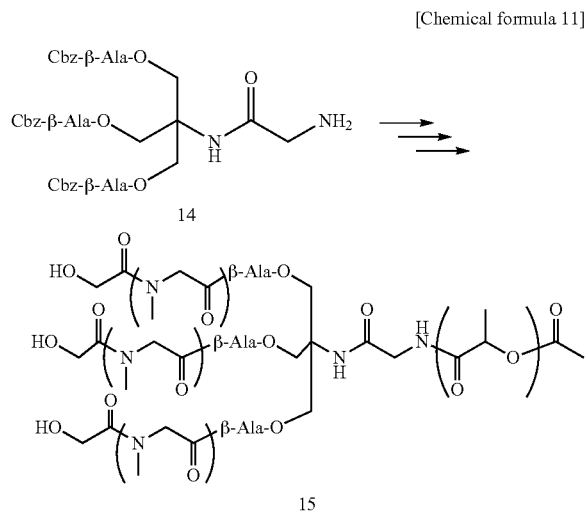

An amphiphilic block polymer 15 was obtained by performing synthesis of a PLLA chain by the polymerization reaction of lactide, removal of Cbz groups for deprotection, protection of the end of the PLLA chain with an acetyl group, synthesis of PS chains by the carboxyanhydride polymerization reaction of sarcosine-NCA, and introduction of carboxyl groups in the same manner as in Example 1 using the amino group-containing compound 14 as an initiator. It is to be noted that in the above formula, numerals indicating the degree of polymerization are omitted.

Example 7

Preparation of Branched Single-Type Molecular Assembly (Preparation of Molecular Assembly from Only Branched-Type Amphiphilic Block Polymer) (2)

In this example, molecular assemblies (polymeric micelles; lactosomes) were prepared from the branched-type amphiphilic block polymer 15 obtained in Example 6 by an injection method and a film method.

[Injection Method]

The branched-type amphiphilic block polymer 15 in an amount of 2 mg was placed in a glass test tube, and dissolved in 0.1 mL of a DMF solution. Ultrapure water in an amount of 1.9 mL was placed in another glass test tube, and the test tube was placed in a water bath at 0° C. while the ultrapure water was stirred for 5 minutes. Then, the DMF solution of the polymer 15 was dispersed in the ultrapure water with stirring, and then further stirred for 5 minutes. The thus obtained particle dispersion liquid was returned to room temperature, and then the organic solvent was removed by treatment with a PD-10 column to prepare a dispersion liquid of a molecular assembly.

[Film Method 1 (Based on Ultrasonic Treatment)]

A dispersion liquid of molecular assembly was prepared in the same manner as in Example 2 except that 2.0 mg of the branched-type amphiphilic block polymer 15 and 2.0 mL of normal saline were used.

[Film Method 2 (Based on Warming Treatment)]

A dispersion liquid of molecular assembly was prepared in the same manner as in the above film method 1 except that the time of ultrasonic treatment in the bath sonicator filled with water at 85° C. was changed to 20 minutes.

[Evaluation of Particle Size]

Figure 11:
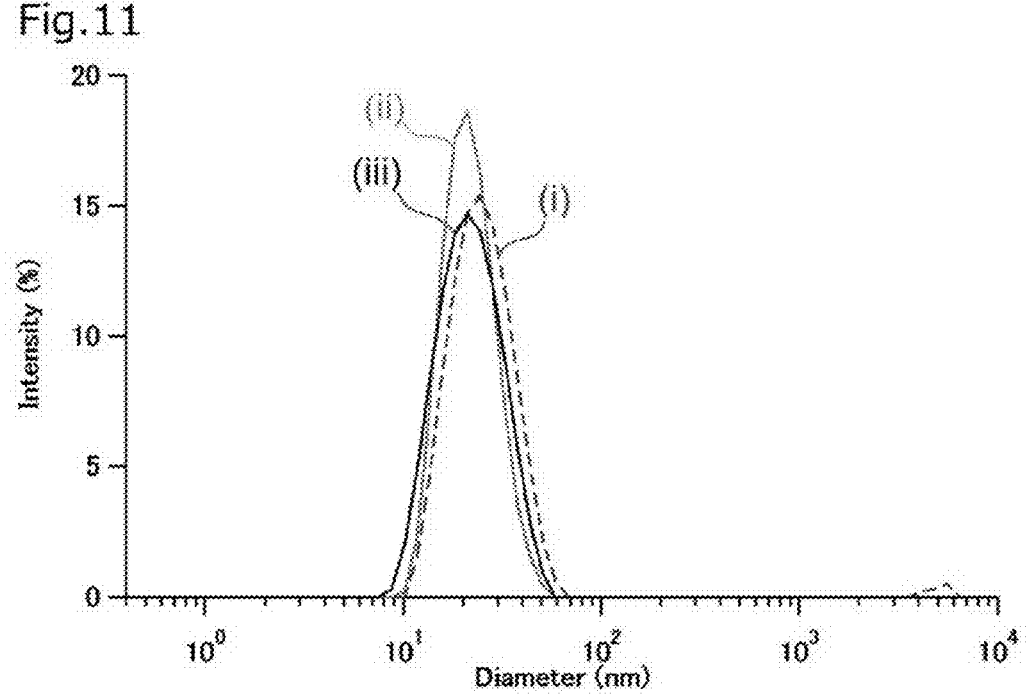
FIG. 11 shows the results of DLS measurement of branched single-type molecular assembly prepared in Example 7 and composed of only a branched-type amphiphilic block polymer.

The obtained dispersion liquids were subjected to particle size measurement, and the results are shown in Table 1 together with polydispersity index (PdI). FIG. 11 shows the dynamic light scattering (DLS) measurement results of particles formed by the injection method (i), particles formed by the film method 1 (ii), and particles formed by the film method 2 (iii). In this example, particles having a particle size of 20 nm to 24 nm were formed.

TABLE 1

| Formation method of particles | Particle size immediately after particle formation (PdI) |
|---|---|
| Injection method (DMF) 0° C. | 23.88 nm (0.157) |
| Film method 1 (Ultrasonic treatment) 85° C., 5 minutes | 20.99 nm (0.140) |
| Film method 2 (Warming treatment) 85° C., 20 minutes | 20.19 nm (0.116) |

Example 8

Synthesis of Branched-Type Amphiphilic Block Polymer (3)

In this example, a branched-type amphiphilic block polymer in which three sarcosines were bound to one end of one polylactic acid chain was synthesized.

[Chemical formula 12]

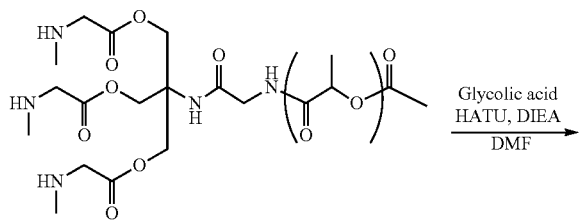

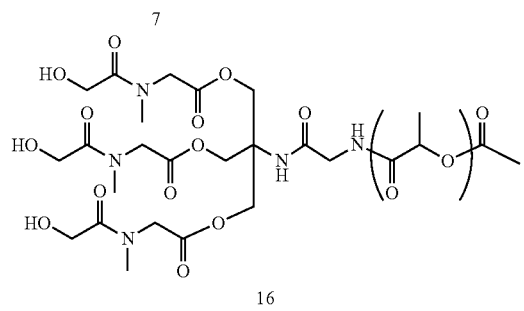

First, a compound 7 was synthesized in the same manner as in Example 1. Then, glycolic acid, HATU, and DIEA were added respectively to the compound 7 to obtain a reaction solution, and the reaction solution was stirred at room temperature for 24 hours. After the completion of reaction, the reaction solution was concentrated and then purified by size exclusion chromatography (Sephadex LH20, eluent: DMF) to obtain a target amphiphilic block polymer 16. It is to be noted that in the above formula, numbers indicating the degree of polymerization of polylactic acid are omitted.

Figure 12:
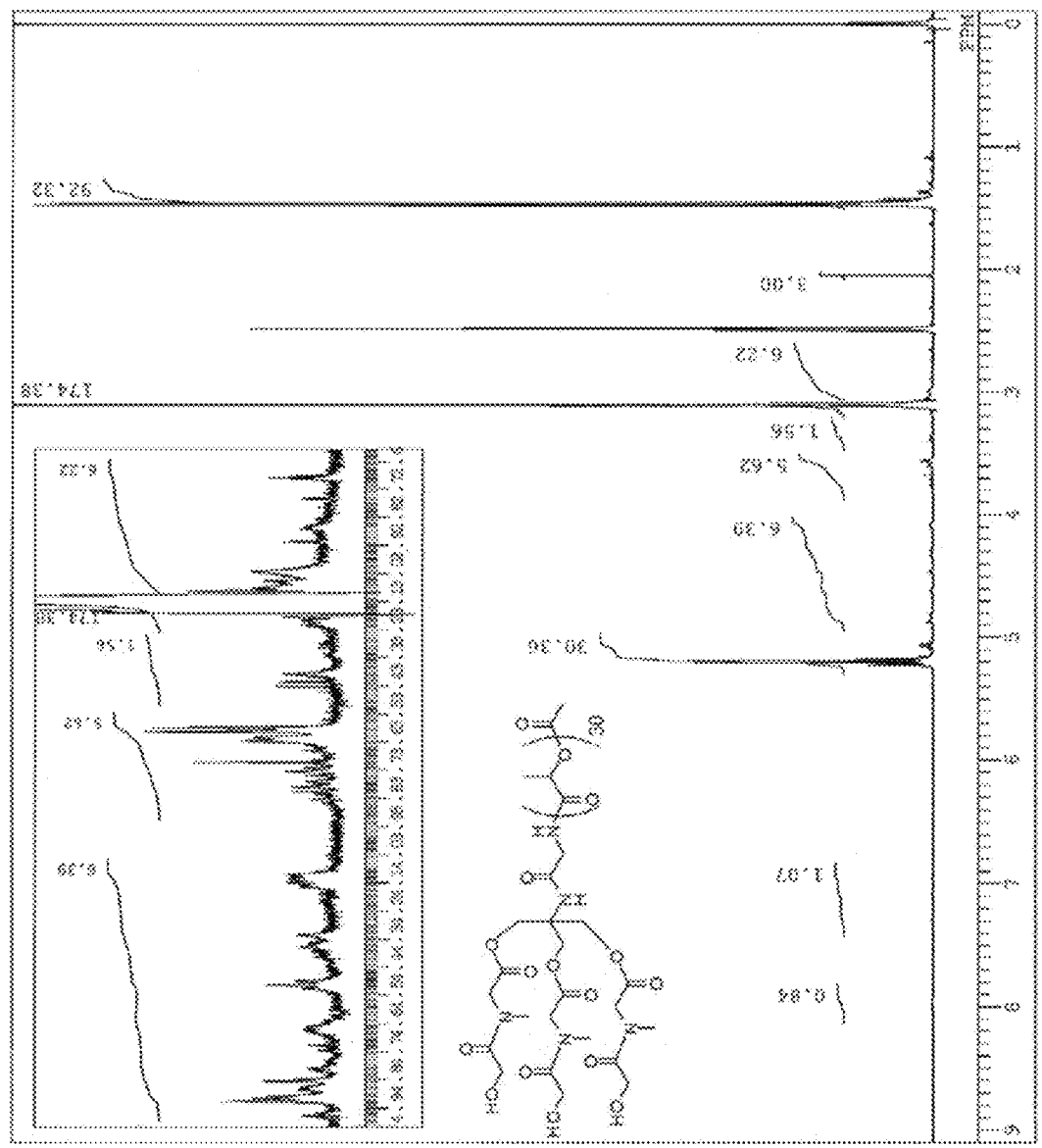
FIG. 12 is a $^1$H NMR spectrum of a branched-type amphiphilic block polymer synthesized in Example 8.

FIG. 12 shows the result of $^1$H NMR measurement of the obtained amphiphilic block polymer 16. From FIG. 12, the composition of the branched-type amphiphilic block polymer obtained in this example was identified, and it was found that the number of lactic acid units in the PLLA chain was 30 and the number of sarcosine units per branch was 1.

Example 9

Preparation of Branched Single-Type Molecular Assembly (Preparation of Molecular Assembly from Only Branched-Type Amphiphilic Block Polymer) (3)

In this example, molecular assemblies (polymeric micelles; lactosomes) were prepared by an injection method from the branched-type amphiphilic block polymer 16 obtained in Example 8.

The same manner as in Example 7 was performed except that the branched-type amphiphilic block polymer 16 was used. Dispersion liquids were obtained in both cases, respectively, one case where the particle formation temperature was 0° C., which was the same as that in Example 7, and the other case where the particle formation temperature was 60° C. instead of 0° C.

The obtained dispersion liquids were subjected to particle size measurement. Then, the dispersion liquids were treated by filtering using a filter with a pore size for removing particles of 200 nm, and were then again subjected to particle size measurement. The particle size measurement results are shown in Table 2 together with polydispersity index (PdI). Further, FIG. 13 shows the results of DLS measurement of particles formed at a temperature condition of 0° C. (i) and particles formed at a temperature condition of 60° C. (ii).

TABLE 2

| Particle formation temperature | Particle size immediately after particle formation (PdI) | Particle size after filter treatment (PdI) |
|---|---|---|
| 60° C. | 77.20 nm (0.134) | 74.79 nm (0.121) |
| 0° C. | 63.29 nm (0.123) | 62.43 nm (0.132) |

Comparative Example 2

Synthesis of Linear Type Amphiphilic Block Polymer and Linear Single-Type Molecular Assembly Prepared Therefrom (2)

Linear type amphiphilic block polymers different in the number of lactic acid units ($N^L$) and the number of sarcosine units ($N^S$) were synthesized, in which one polysarcosine (PS) chain was bound to one polylactic acid (L-polylactic acid; PLLA) chain. A specific synthesis method was the same as that described in Comparative Example 1.

The number of lactic acid units ($N^L$), the number of sarcosine units ($N^S$), and the ratio thereof ($N^S/N^L$) of each of the synthesized linear type amphiphilic block polymers, and the particle size of molecular assemblies are summarized in Table 3. It is to be noted that when particles were not formed from the linear type amphiphilic block polymer, the phrase "no particles were formed" was written in the column instead for particle size. Further, the data of the block polymer whose sample name is "Ref" is a copy of the data of a sample in Entry 1 shown in Table 1 in Chemistry letters, Vol. 36, No. 10, 1220-1221 (2007).

TABLE 3

| No. | Sample Name | $N^L$ | $N^S$ | $N^S/N^L$ | Particle size (nm) |
|---|---|---|---|---|---|
| 1 | SA86-12-1 | 30 | 93 | 3.10 | 34.3 |
| 2 | SA86-8-1 | 30 | 78 | 2.60 | 31.8 |
| 3 | SA86-10-1 | 30 | 75 | 2.50 | 33.8 |
| 4 | SA86-9-1 | 30 | 73 | 2.43 | 32.0 |
| 5 | SA86-5-1 | 30 | 73 | 2.43 | 32.5 |
| 6 | SA86-2-1 | 31 | 75 | 2.42 | 32.8 |
| 7 | SA86-6-1 | 30 | 71 | 2.37 | 37.1 |
| 8 | SA86-19-1 | 30 | 70 | 2.33 | 33.0 |
| 9 | SA86-3-1 | 31 | 71 | 2.29 | 37.4 |
| 10 | SA86-16-1 | 30 | 65 | 2.17 | 31.6 |
| 11 | SA86-17-1 | 30 | 64 | 2.13 | 33.6 |
| 12 | SA86-13-1 | 30 | 63 | 2.10 | 33.3 |
| 13 | SA86-15-1 | 30 | 63 | 2.10 | 32.2 |
| 14 | SA86-18-1 | 30 | 63 | 2.10 | 32.3 |
| 15 | SA16-10-1 | 40 | 76 | 1.90 | 47.1 |
| 16 | SA86-14-1 | 30 | 54 | 1.80 | 41.2 |
| 17 | Ref | 30 | 50 | 1.67 | No particles were formed |
| 18 | SA16-9-1 | 64 | 76 | 1.19 | No particles were formed |
| 19 | SA16-11-1 | 50 | 42 | 0.840 | No particles were formed |

The results indicated that the linear type amphiphilic block polymer composed of polysarcosine and polylactic acid needs to have such composition that a ratio of $N^S/N^L$ of 1.8 or more is achieved in order to form particles from the linear type amphiphilic block polymer.

On the other hand, particles could be formed from the branched-type amphiphilic block polymer according to the present invention (e.g., the compound 16 synthesized in Example 8; $N^S/N^L=0.1$) even when its $N^S/N^L$ ratio was less than 1.8 at which particles could not be formed in this comparative example (Example 9).

The invention claimed is:

1. A branched-type amphiphilic block polymer comprising:
   a branched hydrophilic block comprising sarcosine; and
   a hydrophobic block comprising polylactic acid;
   wherein the branched-type amphiphilic block polymer has a structure represented by the following formula (I):

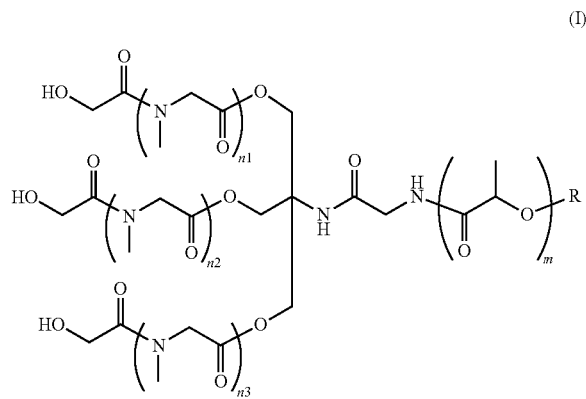

wherein n1, n2 and n3 represent numbers whose sum is 3 to 200, m represents a number of 15 to 60, and R represents a hydrogen atom or an organic group.

2. The branched-type amphiphilic block polymer according to claim 1, wherein a ratio of a total number of the sarcosine units contained in the hydrophilic block to a total number of the lactic acid units contained in the hydrophobic block is 0.05 or more and less than 1.8.

3. A molecular assembly comprising the branched-type amphiphilic block polymer according to claim 1.

4. The molecular assembly according to claim 3, further comprising a linear type amphiphilic block polymer comprising one polysarcosine chain as a hydrophilic block and one polylactic acid chain as a hydrophobic block.

5. The molecular assembly according to claim 3, which encapsulates a functional substance selected from the group consisting of a signal agent and a drug.

6. The molecular assembly according to claim 5, wherein the functional substance has a polylactic acid chain.

7. The molecular assembly according to claim 3, whose particle size is 10 to 50 nm.

8. The molecular assembly according to claim 3, which is obtained by a preparation method comprising the steps of:
   preparing a solution, in a container, containing the branched-type amphiphilic block polymer in an organic solvent;
   removing the organic solvent from the solution to obtain a film comprising the branched-type amphiphilic block polymer on an inner wall of the container; and
   adding water or an aqueous solution into the container and performing ultrasonic treatment to convert the film into a molecular assembly, thereby obtaining a dispersion liquid of the molecular assembly.

9. The molecular assembly according to claim 3, which is obtained by a preparation method comprising the steps of:
   preparing a solution, in a container, containing the branched-type amphiphilic block polymer in an organic solvent;
   dispersing the solution into water or an aqueous solution; and
   removing the organic solvent.

10. A drug delivery system comprising the molecular assembly according to claim 5.

* * * * *